US009259007B2

(12) United States Patent
Asolkar et al.

(10) Patent No.: US 9,259,007 B2
(45) Date of Patent: Feb. 16, 2016

(54) *CHROMOBACTERIUM* FORMULATIONS, COMPOSITIONS, METABOLITES AND THEIR USES

(71) Applicants: Ratnakar Asolkar, Davis, CA (US); James Namnath, Davis, CA (US); Pamela Marrone, Davis, CA (US)

(72) Inventors: Ratnakar Asolkar, Davis, CA (US); James Namnath, Davis, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 14/343,836

(22) PCT Filed: Oct. 23, 2012

(86) PCT No.: PCT/US2012/061503
§ 371 (c)(1),
(2) Date: Mar. 7, 2014

(87) PCT Pub. No.: WO2013/062977
PCT Pub. Date: May 2, 2013

(65) Prior Publication Data
US 2014/0227228 A1 Aug. 14, 2014

Related U.S. Application Data

(60) Provisional application No. 61/551,403, filed on Oct. 25, 2011, provisional application No. 61/551,014, filed on Oct. 25, 2011.

(51) Int. Cl.
*A01N 63/02* (2006.01)
*C12N 1/20* (2006.01)
*A01N 43/90* (2006.01)

(52) U.S. Cl.
CPC ............... *A01N 63/02* (2013.01); *A01N 43/90* (2013.01); *C12N 1/20* (2013.01)

(58) Field of Classification Search
CPC ........... A01N 63/02; A01N 43/90; C12N 1/20
See application file for complete search history.

(56) References Cited

U.S. PATENT DOCUMENTS

| 5,047,424 | A | 9/1991 | Puritch |
| 5,428,175 | A | 6/1995 | Hoshino |
| 6,077,860 | A | 6/2000 | Meunier |
| 6,103,228 | A | 8/2000 | Heins |
| 7,037,494 | B2 | 5/2006 | Mattingly |
| 7,244,607 | B2 | 7/2007 | Martin |
| 2007/0172463 | A1 | 7/2007 | Martin |
| 2009/0111759 | A1 | 4/2009 | Pedersen |
| 2012/0100236 | A1 | 4/2012 | Asolkar |

FOREIGN PATENT DOCUMENTS

| KR | 10-2007-088150 | 8/2007 |
| WO | 91/00012 | 1/1991 |
| WO | 97/15187 A1 | 5/1997 |
| WO | WO 01/74161 | 10/2001 |
| WO | WO 2011/110932 | 9/2011 |
| WO | 2012/061082 A2 | 5/2012 |

OTHER PUBLICATIONS

Steinhaus, "Serratia Marcescens Bizio as an Insect Pathogen" (1959) Hilgardia: vol. 28, No. 14: 351-376.*
U.S. Appl. No. 13/842,981, Flor-Weiler, Not yet published.
Asolkar et al. "Daryamides A-C, Weakly Cytotoxic Polyketides from a Marine-Derived Actinomycete of the Genus *Streptomyces* Strain CNQ-085" J. Nat. Prod. 69:1756-1759. 2006.
Aspelin et al. "Pesticides Industry Sales and Usage, 1996 and 1997 Market Estimates" U.S E.P.A. Publication 733-R-99-001. 1999.
Arena et al. "The Mechanism of Action of Avermectins in Caenorhabditis Elegans: Correlation Between Activation of Glutamate-Sensitive Chloride Current, Membrane Binding and Biological Activity" Journal of Parasitology 81: 286-294. 1995.
Bakhetia et al. "RNA Interference of Dual Oxidase in the Plant Nematode Meloidogyne Incognita" Molecular Plant-Microbe Interactions 18: 1099-1106. 2005.
Balibar et al. "In Vitro Biosynthesis of Violacein from L-Tryptophan by the Enzymes VioA-E from Chromobacterium Violaceurn" Biochemistry 45: 15444-15457, 2006.
Brazilian National Genome Project Consortium, "The Complete Genome Sequence of Chromobacterium Violaceum Reveals Remarkable and Exploitable Bacterial Adaptability," Proc. Natl. Acad. Sci. 100(20)11660-11665. 2003.
Chalvet-Monfray et al. "Synergy Between Deltamethrin and Prochloraz in Bees: Modeling Approach" Environmental Toxicology and Chemistry 15(4): 525-534. 1996.
Chitwood. "Phytochemical Based Strategies for Nematode Control" Annual Review of Phytopathology 40: 221-249. 2002.
Chitwood. "Nematicides" In *Encyclopedia of Agrochemicals*, J. R. Plimmer (ed). New York, John Wiley & Sons. 3: 1104-1115. 2003.
Colby. "Calculating Synergistic and Antagonistic Responses of Herbicide Combinations" Weeds 15(1): 20-22. 1967.
Cronin et al. "Inhibition of Egg Hatch of the Potato Cyst Nematode Globodera Rostochiensis by Chitinase-Producing Bacteria" European Journal of Plant Pathology 103:433-440. 1997.
Dong et al. "Microbial Control of Plant-Parasitic Nematodes: A Five-Party Interaction" Plant Soil 288: 31-45. 2006.
Durán et al. "Biosynthesis of a Trypanocide by Chromobacterium Vialaceum" World Journal of Microbiology and Biotechnology 10:686-690. 1994.
Durán et al. "Chromobacterium Violaceum: A Review of Pharmacological and Industrial Perspectives" Grit. Rev. Microbiol. 27: 201-222. 2001.

(Continued)

Primary Examiner — Robert Yamasaki
Assistant Examiner — Teresa E Knight
(74) Attorney, Agent, or Firm — Chainey P. Singleton; Ying-Horng Liu; Marrone Bio Innovations

(57) ABSTRACT

Stabilized biological pesticides comprising *Chromobacterium* species, filtrate, supernatant, extract or pesticidally active substance derived therefrom with pesticidal activity having improved shelf life due to maintenance of physical uniformity and longer insecticide activity after use due to higher resistance to degradation when exposed to sunlight are disclosed.

10 Claims, 18 Drawing Sheets

(56) References Cited

OTHER PUBLICATIONS

Figure 1:
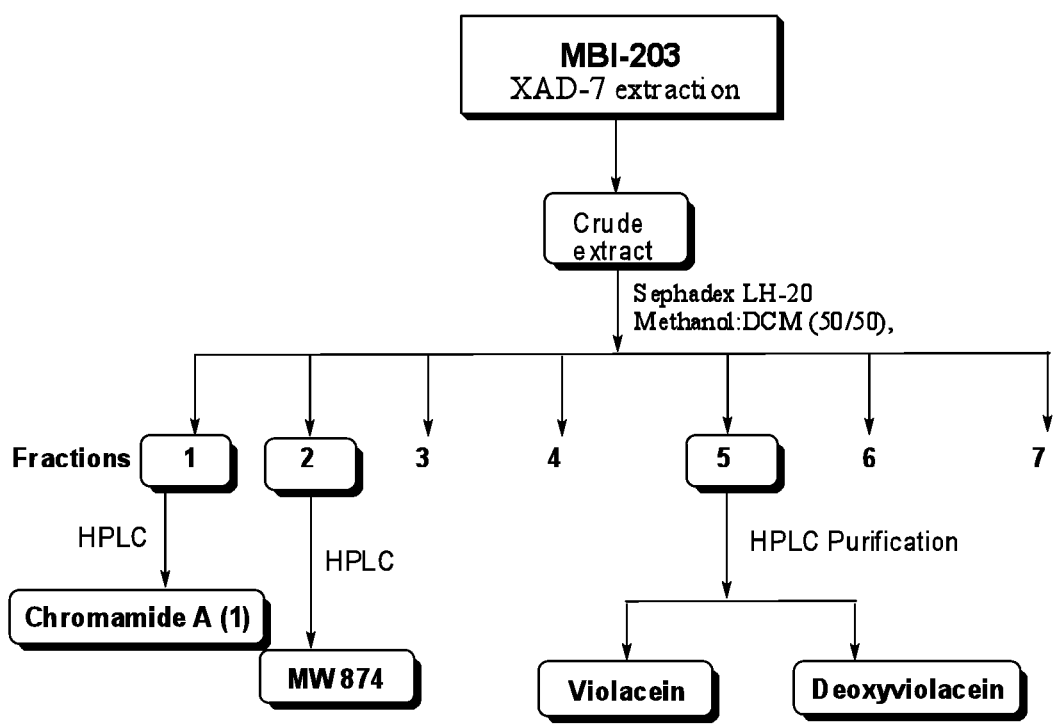

Durán et al. "Violacein: Properties and Biological Activities" Biotechnol. Appl. Biochem. 48: 127-133. 2007.

Durán et al. "Potential Applications of Violacein: a Microbial Pigment" Med. Chem. Res. 21:1524-1532. 2012.

Farenhorst et al. "Synergy in Efficacy of Fungal Entomopathogens and Permethrin Against West African Insecticide-Resistant Anopheles Gambiae Mosquitoes" PLoS One 5(8): e12081. 2010.

Faske et al. "Sensitivity of Meloidogyne Incognita and Rotylenchulus Reniformis to Abamectin" Journal of Nematology 38: 240-244. 2006.

Guerena. "Nematode: Alternative Controls" from www.agrisk.umn.edu/cache/arl02971.htm, ATTRA Publication #IP287. 2006.

Hallmann et al. "Toxicity of Fungal Endophyte Secondary Metabolites to Plant Parasitic Nematodes and Soil-Borne Pathogens" European Journal of Plant Pathology 102: 155-162. 1996.

Hasky-Gunther et al. "Resistance Against the Potato Cyst Nematode Globodera Pallida Systemically Induced by the Rhizobacteria Agrobacterium Radiobacter(G12) and Bacillus Sphaericus (B43)" Fundamentals of Applied Nematology 21: 511-517. 1998.

Hoshino et al. "Biosynthesis of Violacein: Origins of the Hydrogen. Nitrogen and Oxygen Atoms in the 2-Pyrrolidone Nucleus" Agric. Biol. Chem. 51: 2733-2741. 1987.

Hummelbrunner et al. "Acute, Sublethal, Antifeedant, and Synergistic Effects of Monoterpenoid Essential Oil Compounds on the Tobacco Cutworm, Spodoptera Litura (Lep., Noctuidae)" J. Agric, Food Chem. 49(2): 715-720. 2001.

Hungria et al. "Genetic Characterization of Chromobacterium Isolates from Black Water Environments in the Brazilian Amazon" Lett. Appl. Microbiol. 41: 17-23. 2005.

Jaffee et al. "Susceptibility of Root-Knot and Cyst Nematodes to the Nematode-Trapping Fungi Monocrosporium eilipsosporum and M. Cionopagum" Soil Biology and Biochemistry 27: 1083-1090. 1995.

Kämpfer et al. "*Chromobacterium piscinae* Sp. Nov. and *Chromobacterium pseudoviolaceum* Sp. Nov., from Environmental Samples" Int. J. Syst. Evol. Microbiol. 59: 2486-2490. 2009.

Kerry. "Exploitation of the Nematophagous Fungal Verticillium chlamydosporium Goddard for the Biological Control of Root-Knot Nematodes (*Meioidogyne* Spp.)," In *Fungi as Biocontrol Agents: Progress, Problems and Potential*. T. M. Butt, C. Jackson and N. Magan (eds). New York, CAB International, p. 155-168. 2001.

Kirkegaard et al. "Biofumigation Potential of Brassicas" Plant and Soil 201: 71-89. 1998.

Koenning et al. "Survey of Crop Losses in Response to Phytoparasitic Nematodes in the United States for 1994" Supplement to the Journal of Nematology 31(4S): 587-618. 1999.

Kokalis-Burelle et al. "Allelochemicals as Biopesticides for Management of Plant-Parasitic Nematodes." In *Alleolochemicals: Biological Control of Plant Pathogens and Diseases*. Inderjit and K. G. Mukerji (eds). Netherlands, Springer: 15-29. 2006.

Krieg et al. "*Bacillus thuringiensis* var. tenebrionis: A New Pathotype Effective Against Larvae of Coleoptera," Z. Angew. Entomol. 96: 500-508. 1983. (English Abstract).

Martin et al."Bacterial Strains Lethal to Colorado Potato Beetle Larvae," Abstracts of the General Meeting of the American Society for Micorbiology 101:603. 2001.

Martin et al. "Survival of Chromobacterium Violaceum, An Insect Pathogen Under Various Conditions," Abstracts of the General Meeting of the American Society for Microbiology 102:389-390. 2002.

Martin et al. "Characterization of *Chromobacterium* sp., a Purple Bacterium Toxic to Insects," Abstracts of the General Meeting of the American Society for Microbiology 103:Q-226. 2003.

Martin et al. "A Method to Detect Viable, Pigmented Insect Pathogens from Soil," Abstracts of the General Meeting of the American Society for Microbiology 103:Q-436. 2003.

Martin. "A Freeze-Dried Diet to Test Pathogens of Colorado Potato Beetle" Biological Control 29(1): 109-114, 2004.

Martin et al. "*Chromobacterium subtsugae* sp. nov., a Betaproteobacterium Toxic to Colorado Potato Beetle and Other Insect Pests" Int. J. Syst. Evol. Microbiol. 57: 993-999, 2007.

Martin et al. "Toxicity of Chromobacterium Subtsugae to Southern Green Stink Bug (Heteroptera:Pentatomidae) and Corn Rootworm (Coleoptera:Chrysomelidae)" J. Econ. Entomol. 100: 680-684. 2007.

McClean et al. "Quorum Sensing and Chromobacterium Violaceum: Exploitation of Violacein Production and Inhibition for the Detection of N-Acylhomoserine Lactones" Microbiology 143: 3703-3711. 1997.

Meyer et al. "Combinations of Biocontrol Agents for Management of Plant-Parasitic Nematodes and Soilborne Plant-Pathogenic Fungi" Journal of Nematology 34: 1-8. 2002.

Oka et al. "Nematicidal Activity of Essential Oils and their Components Against the Root-Knot Nematode" Phytopathology 90:710-715. 2000.

Oostendorp et al. "In-vitro Interrelationships Between Rhizosphere Bacteria and Heterodera Schachtii" Reviews in Nematology 13: 269-274. 1990.

Quarles (ed.) "2005 Directory of Least-Toxic Pest Control Products." The IPM Practitioner 26:17. 2005.

Roubtsova et al. "Effect of Broccoli (Brassica oleracea) Tissue, Incorporated at Different Depths in a Soil Column, on Meloidogyne incognita" Journal of Nematology 39: 111-117. 2007.

Ryan et al. "Divergent Pathways in the Biosynthesis of Bisindole Natural Products" Chem. Biol. 16: 351-364. 2009.

Sanchez, et al. "Reevaluation of the Violacein Biosynthetic Pathway and its Relationship to Indolocarbazole Biosynthesis" ChemBioChem 7: 1231-1240. 2006.

Sasser et al. "A World Perspective on Nematology: The Role of the Society" In *Vistas on Nematology*. J.A. Veech and D.W. Dickson (Eds.), Society of Nematologists, Hyattsville, MD. p. 7-14, 1987.

Saxena et al. "Bacterial Biocontrol Agents and their Role in Plant Disease Management." In *Biocontrol Potential and its Exploitation in Sustainable Agriculture. vol. 1: Crop Diseases, Weeds, and Nematodes*. R. R. Upadhaya, K. G. Mekerji and B. P. Chamola (eds). New York, Kluwer Academic Plenum Publishers. p. 25-37. 2000.

Shapiro-Ilan et al. "Effects of Combining Microbial and Chemical Insecticides on Mortality of the Pecan Weevil (Coleoptera: Curculionidae)" J. Econ. Entomol. 104(1): 14-20. 2011.

Siddiqui et al. "Biological Control of Plant Parasitic Nematodes by Fungi: a Review" Bioresource Technology 58: 229-239. 1996.

Siddiqui et al. "Role of Bacteria in the Management of Plant Parasitic Nematodes: a Review" Bioresource Technology 69: 167-179. 1999.

Siddiqui et al."Neem Allelopathy and the Root Knot Nematode" The IPM Practitioner 23:9-11. 2001.

Sikora et al. "Biological Control of Plant-Parasitic Nematodes with Plant-Health-Promoting Rhizobacteria" In *Pest Management: Biologically Based Technologies*. Lumsden R.D., Vaughn J.L (eds). Proceedings of Beltsville Symposium XVIII, Washington. American Chemical Society: 166-172. 1993.

Terefe et al. "Effect of a Formulation of Bacillus Firrnus on Root-Knot Nematode Meloidogyne Incognita Infestation and the Growth of Tomato Plants in the Greenhouse and Nursery" Journal of Invertebrate Pathology 100: 94-99. 2009.

Thompson et al. "Spinosad—a Case Study: An Example from a Natural Products Discovery Programme" Pest Manag. Sci. 56: 696-702. 2000.

Whitehead. "Plant-Parasitic Nematodes, Their Importance and Control," In *Plant Nematode Control*. Wallingford, UK, CAB International: p. 1-12, 1998.

Wirth et al. "Synergy Between Toxins of *Bacillus thuringiensis* subsp. Israelensis And Bacillus Sphaericus" J. Med. Entomol. 41: 935-941. 2004.

Young et al. "*Chromobacterium aquaticum* sp. nov., Isolated from Spring Water Samples" Int. J. Syst. Evol. Microbiol. 58: 877-880. 2008.

Zeck. "A Rating Scheme for Field Evaluation of Root-Knot Nematode Infestations" Pflanzenschutz-nachrichten Bayer 24(1): 141-144. 1971.

International Search Report and Written Opinion issued in PCT App. No. PCT/US2011/057541 dated Jun. 26, 2012.

(56) References Cited

OTHER PUBLICATIONS

Extended European Search Report (EP 12842863.8) dated May 5, 2015.
Martin, Phyllis A. W. et al., "*Chromobacterium subtsugae* sp. nov., a betaproteobacterium toxic to Colorado potato beetle and other insects," (2007) International Journal of Systematic and Evolutionary Microbiology 57:993-999.
Martin, Phyllis A. W. et al., "Toxicity of Chromobacterium subtsugae to Southern Green Stink Bug (Heteroptera: Pentatomidae) and Corn Rootworm (Coleoptera: Chrysomelidae)", (2007) J. Econ. Entomol. 100(3):680-684.

* cited by examiner

Chromamide A (1)

Violacein (2)

Deoxyviolacein (3)

CHROMOBACTERIUM FORMULATIONS, COMPOSITIONS, METABOLITES AND THEIR USES

TECHNICAL FIELD

Provided is the use of or compositions or formulations comprising *Chromobacterium* species, filtrate, supernatant, extract, pesticidally active compound or metabolite derived therefrom as an acaricide and insecticide, particularly against infestation of one or more pests belonging to the Acarina, Scarabeidae, Drosophilidae, TriozidaeAphidae, Muscidae, Anthomyiidae or Tenebrionidae families. Further provided are biological pesticide (also referred to as biopesticide) formulations, particularly those comprising *Chromobacterium* species, filtrate, supernatant, extract, metabolites or pesticidally active compounds derived therefrom, methods for producing them and methods of use as modulating pest infestation. More specifically, provided are stabilized biological pesticides having improved shelf life due to maintenance of physical uniformity and longer insecticide activity after use due to higher resistance to degradation when exposed to sunlight.

BACKGROUND

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. There are several well-known examples of microbial natural products that are successful as agricultural insecticides (Thompson et al., 2000; Arena et al., 1995; Krieg et al. 1983).

The development of a microbial pesticide starts with the isolation of a microbe in a pure culture. It then proceeds with efficacy and spectrum screening using in vitro, in vivo or pilot scale trials in a greenhouse and in the field. At the same time, active compounds produced by the microbe are isolated and identified. For the commercialization of a microbial pesticide, the microbe has to be economically produced by fermentation at an industrial scale and formulated with biocompatible and approved additives to increase efficacy and to maximize the ease of application as well as storage stability under field conditions.

*Chromobacterium*

In 2000, Dr. Martin and her coworkers at USDA isolated a purple-pigmented bacteria (PRAA4-1) from a forest soil in Maryland (Martin et al., 2007a). In the initial screening, they found this bacteria to be toxic to Colorado potato beetle and other insect pests (Martin et al., 2007b). This motile, Gram-negative, bacteria was identified as a new species of Chromobacteria, *Chromobacterium substsugae* sp. nov (Martin et al., 2007c). It is a facultatively aerobic, motile, Gram-negative betaproteobacterium with polar flagella. Colonies formed at 2-3 days on an L-agar plate at 25° C. are initially cream colored, gradually turning light to dark violet during the following 24 hours. Colonies of PRAA4-1 grow well on peptone based media with an optimum at 25° C., pH 6.5-8.0, and with 0-1.5% (w/v) NaCl (Martin et al., 2007a).

Since the finding of *C. substugae* by Martin and her coworkers, at least three new species of Chromobacteria have been isolated, and characterized; Young et al. (2008) isolated a novel *Chromobacterium* species, *C. aquaticum*, from spring water samples in Taiwan, and Kampfer et al. (2009) isolated two species, *C. piscinae* and *C. pseudoviolaceum*, from environmental samples collected in Malaysia.

Of all known species of Chromobacteria, *C. violaceum*, a gram-negative saprphyte from soil and water. Published information on secondary metabolites produced by Chromobacteria is based on studies on *C. violaceum* only (see, for example, Duràn and Menck (2001) for a comprehensive review of the pharmacological and industrial perspectives of *C. violaceum*). It is normally considered nonpathogenic to humans, but as an opportunistic pathogen, it has occasionally been the causative agent for septicemia and fatal infections in humans and animals. *C. violaceum* is known to produce a purple pigment, violacein, which is a bisindole molecule generated by a fusion of two L-tryptophan molecules in the presence of oxygen (Hoshino et al., 1987; Ryan and Drennan; 2009). Violacein biosynthesis is regulated by quorum-sensing, a common mechanism regulating various other secondary metabolism pathways in Gram-negative bacteria (Mc-Clean et al., 1997).

Other known metabolites of *C. violaceum* summarized by Duràn and Menck (2001) include hydrogen cyanide, ferrioxamine E, B-lactamic glycopeptides SQ28,504 and SQ28,546, antibiotics such as aerocyanidin, aerocavin, 3,6-dihydroxy-indoxazene, and monobactam SB-26.180, and an antitumoral depsipeptide FR901228. According to the review article by Duràn and Menck (2001), *C. violaceum* also produces unusual sugar compounds such as extracellular polysaccharides and lipopolysaccharides.

US patent application publication no. US20120100236 also discloses compounds obtainable or derived from *Chromobacterium* species, more particularly, *Chromobacterium substugae*.

Mites and Acaricides

*Tetranychus urticae* (Two spotted spider mite) is a member of the Tetranychidae family Spider mites are perhaps the most important mite pests of ornamentals. They also cause considerable damage in more than 180 species of greenhouse and field crops. These mites are also among the most difficult arthropod pests to control and resistance to chemicals can develop quickly (Stamps and Osborne 2009, Osborne, Ehler and Nechols, 1999).

Acaricides are compounds that kill mites (miticides) and ticks (ixodicides). This class of pesticides is large and includes antibiotics, carbamates, formamidine acaricides, pyrethroids, mite growth regulators, and organophosphate acaricides. Besides chemical pesticides, diatomaceous earth and fatty acids can be used to control mites. They typically work through disruption of the cuticle, which dries out the mite. In addition, some essential oils such as peppermint oil, are used to control mites. In spite of the great variety of known acaricide compounds, mites remain a serious problem in agriculture because of the damage they cause to the crops. They can produce several generations during one season, which facilitates rapid development of resistance to the acaricide products used. Hence, new pesticide products with new target sites and novel modes of action are critically needed.

House Flies

*Musca domestica* (House flies) are members of the family Muscidae. This family is considered an economic problem domestically and worldwide. Other members of the Muscidae family include face fly, stable fly, and horn fly. They are considered a nuisance and are vectors of human and animal diseases. Their habits of walking and feeding on garbage and excrement and on the humans and food make them ideal agents for the transfer of disease organisms. This species can also be a pest to animals and transmit disease through open wounds.

Plant Feeding Flies—Spotted Wing *Drosophila*

The spotted wing *Drosophila, Drosophila suzukii* is a recent invader to the fruit and vegetable growing areas in the United States. It is far more destructive than a well known related species *Drosophila melanogaster* and other *Drosophila* because *D. suzukii* can feed on and damage in-tact fruits and vegetables, while other *Drosophila* only feed on decaying plant material.

Root Maggots

Root maggots of the family Anthomyidae feed on the roots of several different plants. Cabbage Root Maggots affect cabbage, cauliflower, broccoli, and Brussels sprouts. (This group of vegetables is also known as 'cole crops'). Different types of root maggots also occur that affect carrots, onions, and other vegetable crops. Because cole crops are cool-season vegetables, Cabbage Root Maggots are much more prominent in Northern zones of the US. They are difficult to control, because they hatch and feed underneath the soil, so you may only know they are there when you notice stunted growth or wilting foliage.

Green Peach Aphids

*Myzus persicae*, (green peach aphids) are members of the Aphididae family (see US20110054022). As evident by its common name, green peach aphids are pests of a wide range of fruits, vegetables and ornamental plants and have a worldwide presence. These insects are particularly harmful since they not only cause direct damage by feeding on phloem sap but are also potential vectors for the plum pox virus, the causal agent for Sharka disease, which causes fruit deformation and discoloration. As a result, infected trees must be uprooted. Attempts have been made to control these pests with various pesticides. However, resistance is often developed.

Potato Psyllid

*Bactericera cockerelli*, (potato psyllid) is a member of the Triozidae family and is a causative agent of zebra chip disease via infestation of gram negative bacteria. Although it is native to North America, it has been found in New Zealand as well (www.biosecurity.govt.nz/files/pests/potato-tomato-psyllid/psvillid-factsheet.pdf). The potato psyllid generally breeds in solanaceous hosts (such as tomatoes and potatoes). However, they have been found in other plants as well such as capsicum, chilli, eggplant, kumara, poroporo, tamarillo and thornapple.

Litter Beetles

*Alphitobius diaperinus* is a serious pest in the poultry industry and is a member of the Tenebrionidae family. The Bt strain PS86B1 reportedly has activity against *Alphitobius* (U.S. Pat. No. 5,100,665 to Hickle et al.). *Bt tenebrionis* may have activity against larvae of this beetle as well (U.S. Pat. No. 5,244,660). Litter beetles and a few other coleopteran species act as vectors for protozoan, bacterial, and viral diseases of chickens and turkeys resulting in significant economic loss. Litter beetles act as a significant reservoir for pathogenic *Salmonella* species including the more pathogenic varieties, such as *S. enterica* serotype *enteritidis*. The problem is that poultry contaminated with pathogenic organisms like *Salmonella* threaten human health. These beetles inhabit the litter, wood, Styrofoam, fiberglass, and polystyrene insulation panels of chicken houses. Larvae and adult beetles thrive both on bird droppings and on grains used as chicken feed. These large beetle populations and their diverse habitats within chicken houses make it more difficult to eradicate the *Salmonella* they carry. In the midst of a heavy litter beetle infestation, or prior to establishing new chicken populations neither frequent changes in the litter nor dusting with multiple chemical insecticides is a completely effective control for this pest.

Grubs and Scarabs

Grubs, such as white grubs (*Cyclocephala lurida*), Southern Masked Chafer, (*Rhizotrogus majalis*) Japanese beetle larvae, (*Popillia japonica*) black vine weevil larvae (*Otiorhynchus sulcatus*), oriental beetle larvae (*Anomala orientalis*), members of the Scarabaeidae family, have been found to infest turf and pasture grasses. Adult scarabs have been found to infest ornamental plants, and numerous crops around the world. Various pesticides have been tried and include chemical pesticides, nematodes (see, for example, U.S. Pat. No. 7,641,573) and *Bacillus thuringiensis* (see U.S. Pat. No. 5,185,158), peromones, and natural repellents such as catnip and chives.

Polyhydroxyalkanoates (PHAs)

Bio-plastic is defined as a form of plastic synthesized from renewable resources such as plant starch and microbial species. Some of the biodegradable plastic materials under development include polyhydroxyalkanoate (PHA), polylactide, aliphatic polyesters, polysaccharides, and the copolymers and/or blends of these. PHAs in particular include several polymeric esters such polyhydroxybutyrates, polyhydroxybutyrate co-hydroxyvalerates (PHBV), polyhydroxybutyrate co-hydroxyhexanoate (PHBHx) and polyhydroxybutyrate co-hydroxyoctonoate (PHBO). Poly3-hydroxybutyric acid (PHB) is the most common natural microbial PHA. Polyhydroxyalkanoates are 100% biodegradable polymers. Since they have similar properties to various synthetic thermoplastic like polypropylene, PHAs can be used in their place. They are also totally degraded to water and carbon dioxide under aerobic conditions and to methane under anaerobic conditions by micro-organisms in soil, lake water, sewages and sea water. Depending on the number of carbon atom in the chain, PHAs have been divided into two groups: short-chain length (SCL) which consists of 3-5 carbon atoms, and medium-chain length (MCL) which consists of 6-14 carbon atoms (Khanna S, Srivastava A K. 2005). These differences are mainly due to the substrate specificity of the PHA synthases that can accept 3HAs of a certain range of carbon length. The other well-known PHA$_{SCL}$ is the copolymer, poly(3-hydroxy-butyrate-co-3-hydroxyvalerate) P(3HB-co-3HV), which comprise of four- and five-carbon monomeric units. The proportion of these monomeric units can vary, and this affects the physical properties of the polymer, i.e. less brittle with increasing proportion of 3HV unit.

In some microbial species, accumulation of PHA occurs during the presence of excess carbon and a limitation of nitrogen sources (Verlinden et al., 2007). PHAs produced in response to stressful conditions serve as energy storage molecules to be utilized when common energy sources are absent (Solaiman and Ashby, 2005). The plastic polymers accumulate intracellularly as light refracting amorphous storage granules in these organisms (Mukhopadhyay et al., 2005). PHB is synthesized from acetyl-CoA using three enzymatic steps (Krans et al., 1997). From a biotechnological point of view, the ability of bioplastics to be biodegradable makes them a desirable substitute for petrochemical-based plastic, an environmental pollutant (Lee, 1996). Increased production of bioplastics can significantly reduce carbon dioxide emissions, curtail plastic waste generation and decrease consumption of fossil fuels.

PHAs can be obtained from the following three methods: biosynthesis by microorganisms, photosynthesis by transgenic plants, and in vitro biosynthesis using appropriate enzymes (see, for example, U.S. Pat. No. 7,455,999, WO9914313). In most bacteria, cells synthesize PHA under growth-limiting substrates other than carbon source such as nitrogen, phosphorus or oxygen.

Accumulated PHA serves as both carbon and energy source during starvation. PHA also serves as a sink for reducing power and could therefore be regarded as a redox regulator within the cell. PHAs are also useful as stereo regular compounds which can serve as chiral precursors for the chemical synthetic of optically active compounds. Such compounds are particularly used as biodegradable carriers for long-term dosage of drugs, medicines, hormones, insecticides and herbicides (Reddy 2003). They are also used as osteosynthetic materials in the stimulation of bone growth owing to their piezoelectric properties, in bone plates, surgical sutures and blood vessel replacements (Schaefer et al., 2000). Furthermore, there have been disclosures of method of copolymer production by microbiological process using various bacteria e.g. *Alcaligenes eutrophus* NCIMB 40124 (EP. 0431883A2) and U.S. Pat. No. 7,455,999. EP No. 2236089A1 discloses uses of these polymers in multizone implants for orthopedic repair devices and soft tissue fixation devices. WO 91/00917A1 discloses method for controlling and modifying novel polyester biopolymer by manipulation of the genetics and enzymology of synthesis of polyhydroxybutyrate (PHB) and polyhydroxyalkanoate (PHA) polyesters at the molecular level in prokaryotic and eukaryotic cells, especially plants. WO 2005/030482A1 discloses methods and uses as compostable packing materials. WO2008/110541 discloses the method of stabilization of polyhydroxybutyrates against thermal degradation.

Lignin

Lignin is a principal constituent of the woody structure of higher plants. Processed lignin is obtained as a by-product of wood pulping reactions. Lignin products include, for example, lignin sulphonates, alkali lignins, and oxylignins which may be obtained from sulphite, sulphate, and alkali waste liquors (Snook, 1982, Handbook for Pulp & Paper Technologists, TAPPI, Atlanta).

Lignin has been found to have a variety of commercial uses. For example, alkali soluble lignin has been used as a dispersing agent. U.S. Pat. No. 3,726,850 discloses the use of an alkali soluble, ozone-treated lignin product, which is essentially free of organically bound sulfur, as a dispersing agent for clays, dyestuffs, pesticides, carbon black and other materials. U.S. Pat. No. 4,666,522 discloses the use of lignosulphonate products for preparing emulsions of waxes, oils, fats, asphalts, and mixtures thereof. Lignin acetate, has been reported to be useful for applications such as acting as a binder in water-based printing ink compositions. (See, e.g., U.S. Pat. No. 4,612,051). U.S. Pat. No. 5,668,183 discloses the use of lignin sulphonate products for dispersing fat-soluble substances. Furthermore, there have been disclosures of binding of lignin-pesticide complexes (see, for example, U.S. Pat. No. 3,813,236, U.S. Pat. No. 3,929,453, reissued as Re. U.S. Pat. No. 29,238, U.S. Pat. No. 4,381,194, US Patent Application Pub. No. 20110015237, US Patent Application Pub. No. 2010136132, US Patent Application Pub. No. 20100278890, US Patent Application Pub. No. 20080113920, US Patent Application Pub. No. 2006247130, U.S. Pat. No. 7,867,507, WO2003/005816, U.S. Pat. No. 5,994,266).

Sodium Benzoate

Sodium benzoate has been used in various formulations as an anti-microbial in food preparations. For example, U.S. Pat. No. 6,599,514 discloses synergistic antifungal compositions comprising an antifungal agent and a food additive, which produces a synergistic effect on the overall antifungal activity of the antifungal composition. Food additives disclosed in U.S. Pat. No. 6,599,514 included sorbic acid and sorbates, benzoic acid and benzoates, hydroxy-benzoates, sulphur dioxide and sulphites, biphenyl and derivatives, nitrites, nitrates, lactic acid, lactates, citric acid and citrates, tartaric acid and tartrates, orthophosphoric acid and orthophosphates, malates, adipic acid, succinic acid, 1,4-heptonolactone, nicotinic acid, triammoniun citrate, ammonium ferric citrate, calcium disodium EDTA, glycerol, di-, tri- and polyphosphates, fatty acids (E470), mono- and diglycerides of fatty acids (E471), esters of mono- and diglycerides of fatty acids, carbonates, gluconates, chlorine (E92S), sodium hexametaphosphate, butylated hydroxyanisole (BHA), butylated hydroxy toluene (BHT) (E321), t-butyl hydroquinone (THBQ), propyl gallate, calcium heptonate, calcium phytate, diethyl ether, EDTA, disodium dihydrogen EDTA, ethyl acetate, glycerol mono-, di- and triacetates, glycine, oxystearin, propan-1,2-diol and propan-2-01 and sodium heptonate.

Sodium benzoate has also been used in pesticide formulations. For example, U.S. Pat. No. 4,668,507 by SC Johnson teaches use of sodium benzoate in pesticides contained in pressurized steel aerosol delivery systems where main mode of stabilization is corrosion inhibition. U.S. Pat. No. 5,620,678 discloses an insecticide formulation that include sodium benzoate as corrosion inhibitor. U.S. Pat. No. 4,731,379 teaches insecticidal compositions that contain sodium benzoate when used as an animal shampoo to kill fleas. In this patent the use of sodium benzoate is not shown to increase effectiveness of the insecticide or stabilize the product but rather, is thought to assist in healing of wounds of the treated animal. U.S. Pat. No. 5,017,620 teaches insecticidal compositions that contain sodium benzoate and other known preservatives when used as an anti-microbial to stabilize the product while in storage. U.S. Pat. No. 6,841,572 discloses an aqueous solution for treating live plants, crops, trees, pre-harvest fruits, vegetables, leaves, stems, roots and flowers having a pH of between 4.0 and 6.5 and consisting essentially of fungicidally and/or bactericidally effective concentrations of one or more preservative compounds selected from the group consisting of sorbic, benzoic and lactic acid; the sodium, potassium, calcium and ammonium salts of benzoic, sorbic, hydroxymethyl glycinic, lactic and propionic acid; and methyl, ethyl, propyl and buryl paraben, at least one anionic surfactant, and optionally an acidulant.

SUMMARY

Provided are compositions and methods for modulating and/or infestation of one or more Acari (arachnid), Muscidae, Drosophilidae, Anthomyidae, Aphididae, Triozidae, Tenebrionidae and/or Scarabaiedae pests comprising or using a supernatant, filtrate and/or extract and/or one or more metabolites from said supernatant, filtrate and/or extract of a strain of *Chromobacterium* sp., particularly a violacein producing strain, including but not limited to *Chromobacterium piscinae, C. pseudoviolaceum, Chromobacterium substugae* and more particularly, a strain of *Chromobacterium substugae* sp. nov. and even more particularly a strain of *Chro-* mobacterium substugae sp. nov. having the identifying characteristics of NRRL B-30655 described in U.S. Pat. No. 7,244,607.

Specifically provided is a method for modulating infestation of arachnid (Acari or Acarina) and/or one or more insect pests belonging to the Anthomyidae, Drosophilidae, Muscidae, Aphididae, Triozidae, Tenebrionidae or Scarabaiedae family in a location where modulation is desired an amount of (a) a supernatant, filtrate and/or extract and/or one or more metabolites from said supernatant, filtrate and/or extract of a strain of *Chromobacterium* sp. and (b) another pesticidal substance, particularly, an acaracide and/or insecticide which may be effective against Acari and/or one or more insect pests belonging to the Anthomyidae, Drosophilidae, Muscidae, Aphididae, Triozidae, Tenebrionidae or Scarabaiedae family effective to modulate infestation of arachnid and/or one or more insect pests belonging to the Anthomyidae, Drosophilidae, Muscidae, Aphididae, Triozidae, Tenebrionidae or Scarabaiedae family at said location.

In a specific embodiment, the Acari infestation is Tetranychidae (mite) infestation. In a more specific embodiment, the mite infestation is *Tetranychus urticae* infestation.

In another specific embodiment, the insect pest infestation is a *Musca* sp., *Myzus* sp., *Bactericera* sp., *Cyclocephala* sp. or *Alphitobius* sp. *Drosophila* sp. *Delia* sp., *Rhizotrogus* sp. *Popillia* sp., *Anomala* sp. or *Otiorhynchus* sp. infestation. In an even more specific embodiment, the insect pest infestation is a *Musca domesitcas* (house fly), *Drosophila suzukii* (Spotted Wing *Drosophila*), *Delia radicum* (cabbage root maggot), *Myzus persicae* (green peach aphid), *Bactericera cockerelli* (potato psyllid), *Alphitobius diaperinusxi* (litter beetle), *Cyclocephala lurida* (white grub), *Rhizotrogus majalis* (Southern Masked Chafer), *Popilla japonica* (Japanese beetle), *Otiorhynchus sulcatus* (black vine weevil), *Anomala orientalis* (oriental beetle).

Also provided herein is a pesticidal combination which modulates infestation of at least one arachnid and/or one or more insect pests belonging to the Acari, Anthomyidae, Drosophilidae, Muscidae, Aphididae, Triozidae, Tenebrionidae or Scarabaiedae family comprising as active components: (a) a supernatant, filtrate and/or extract of *Chromobacterium* sp. and/or one or more metabolite(s) from said supernatant, filtrate and/or extract of *Chromobacterium* sp. and (b) another pesticidal substance, particularly, an acaracide and/or insecticide which may be effective against one or more insect pests belonging to the Acari, Anthomyidae, Drosophilidae, Muscidae, Aphididae, Triozidae, Tenebrionidae or Scarabaiedae family wherein (a) and (b) may optionally be present in synergistic amounts. The pesticidal substance may be (a) derived from a microorganism; (b) a natural product and/or (c) a chemical pesticide and in particular a chemical insecticide.

In one embodiment, the metabolite may be a compound that (a) has pesticidal activity; (b) has a molecular weight of about 840-900 as determined by Liquid Chromatography/Mass Spectroscopy (LC/MS) and (c) has an High Pressure Liquid Chromatography (HPLC) retention time of about 7-12 minutes on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm and (d) is optionally obtainable from a *Chromobacterium* species. The compound in one embodiment may be a peptide.

In a particular embodiment, the compound has 43 carbons, seven methyl, ten methylene carbons, twelve methines, 6 olefinic methines, and eight quaternary carbons as determined by $^{13}C$ NMR. In more particular embodiments, the compound encompasses compounds "A", "B", "C", "D", depicted as ##STR001#. ##STR001a##, ##STR001b##, ##STR001c## respectively.

In one specific embodiment, the compound "A": (a) is obtainable from a *Chromobacterium* species; (b) is toxic to a pest; (c) has a molecular weight of about 840-890 and more particularly, 860 as determined by Liquid Chromatography/Mass Spectroscopy (LC/MS); (d) has $^1H$ NMR values of δ 8.89, 8.44, 8.24, 8.23, 7.96, 7.63, 6.66, 5.42, 5.36, 5.31, 5.10, 4.13, 4.07, 4.05, 3.96, 3.95, 3.88, 3.77, 3.73, 3.51, 3.44, 3.17, 2.40, 2.27, 2.11, 2.08, 2.03, 2.01, 1.97, 1.95, 1.90, 1.81, 1.68, 1.63, 1.57, 1.53, 1.48, 1.43, 1.35, 1.24, 1.07, 1.02, 0.96, 0.89, 0.88, 0.87, 0.80 and has $^{13}C$ NMR values of δ 173.62, 172.92, 172.25, 172.17, 171.66, 171.28, 170.45, 132.13, 130.04, 129.98, 129.69, 129.69, 125.48, 98.05, 70.11, 69.75, 68.30, 68.25, 64.34, 60.94, 54.54, 52.82, 49.72, 48.57, 45.68, 40.38, 39.90, 38.18, 36.60, 31.98, 31.62, 31.58, 29.53, 28.83, 27.78, 24.41, 23.06, 22.09, 20.56, 19.31, 18.78, 17.66, 15.80 (e) has an High Pressure Liquid Chromatography (HPLC) retention time of about 7-12 minutes, more specifically about 9 minutes and even more specifically about 9.08 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm.

In another specific embodiment, the compound "B" has the following characteristics: (a) is obtainable from a *Chromobacterium* species; (b) is toxic to a pest; (c) has a molecular weight of about 850-900 and more particularly, 874 as determined by Liquid Chromatography/Mass Spectroscopy (LC/MS); (d) has an High Pressure Liquid Chromatography (HPLC) retention time of about 7-12 minutes, more specifically about 9 minutes and even more specifically about 9.54 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm.

The metabolite may also be a compound including but not limited to:

(A) a compound having the structure ##STR001##

STR001##

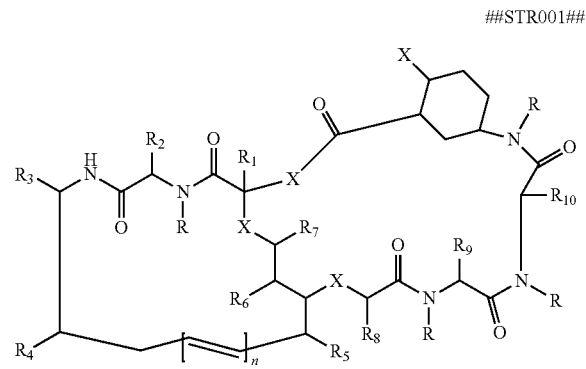

or a pesticidally acceptable salt or stereoisomers thereof, wherein R is —H, lower chain alkyl containing 1, 2, 3, 4, 5, 6, 7, 8 or 9 alkyl moieties, aryl or arylalkyl moiety, substituted lower alkyl; X is O, NH, NR or S; n is 0, 1, 2, 3, 4, 5, 6, 7, 8 or 9; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(B) a compound having the structure ##STR001a##

STR001a##

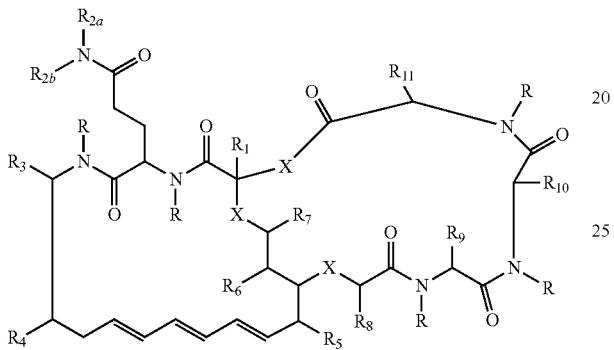

wherein R is —H, lower chain alkyl containing 1, 2, 3, 4, 5, 6, 7, 8 or 9 alkyl moieties, aryl or arylalkyl moiety, substituted lower alkyl; X is O, NH, NR or S; $R_{2a}$, $R_{2b}$ are independently selected from the group consisting of —H, alkyl, lower-alkyl, substituted alkyl and substituted lower-alkyl; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

(C) a compound having the structure ##STR001b##

STR001b##

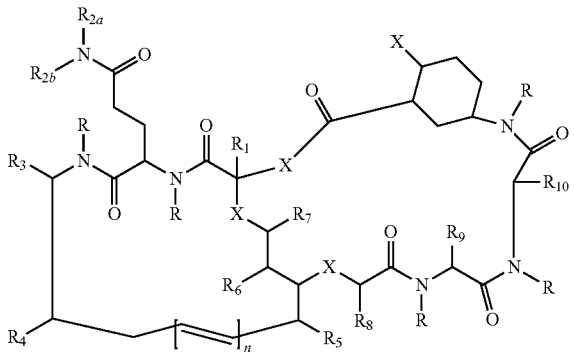

wherein R is —H, lower chain alkyl containing 1, 2, 3, 4, 5, 6, 7, 8 or 9 alkyl moieties, aryl or aryl alkyl moiety, substituted lower alkyl; X is O, NH, NR or S; n is 0, 1, 2, 3, 4, 5, 6, 7, 8 or 9; $R_{2a}$, $R_{2b}$ are independently selected from the group consisting of —H, alkyl, lower-alkyl, substituted alkyl and substituted lower-alkyl; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

(D) a compound having the structure ##STR001c##

STR001c##

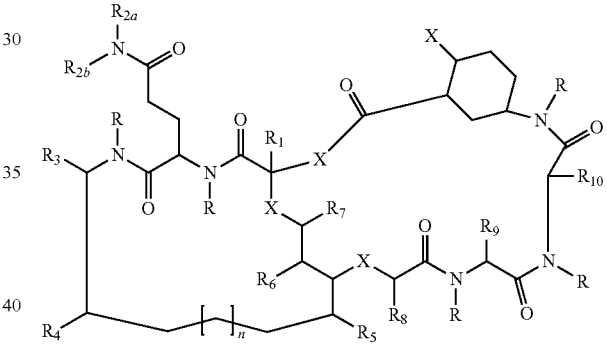

wherein R is —H, lower chain alkyl, aryl or aryl alkyl moiety, substituted lower alkyl containing 1, 2, 3, 4, 5, 6, 7, 8 or 9 alkyl moieties; X is O, NH, NR or S; n is 0, 1, 2, 3, 4, 5, 6, 7, 8 or 9; R2a, R2b are independently selected from the group consisting of —H, alkyl, lower-alkyl, substituted alkyl and substituted lower-alkyl; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In a more particular embodiment, the metabolite is chromamide A (1).

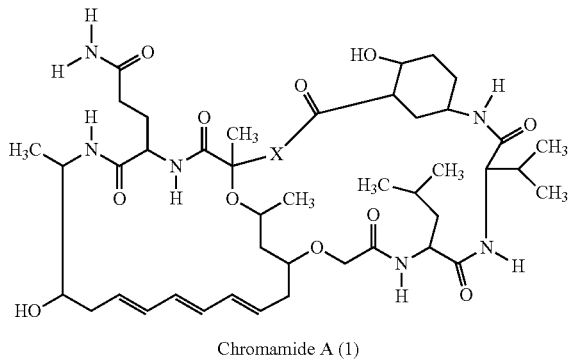

Chromamide A (1)

In a particular embodiment, the metabolite is compound "C", has the following characteristics: (a) is obtainable from a *Chromobacterium* species; (b) is toxic to one or more pests; (c) has a molecular weight of about 325-360 and more particularly, about 343 as determined by Liquid Chromatography/Mass Spectroscopy (LC/MS); (d) has an High Pressure Liquid Chromatography (HPLC) retention time of about 8-14 minutes, more specifically about 10 minutes and even more specifically about 10.88 min on a reversed phase C-18 HPLC (Phenomenex, Luna 5/t C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm. In a particular embodiment, compound "C" may be violacein (2), a known compound isolated earlier from *Chromobacterium violaceum*.

In another embodiment, another metabolite used in the compositions and methods set forth above, is the compound "D", has the following characteristics: (a) is obtainable from a *Chromobacterium* species; (b) is toxic to a pest; (c) has a molecular weight of about 315-350 and more particularly, about 327 as determined by Liquid Chromatography/Mass Spectroscopy (LC/MS); (d) has an High Pressure Liquid Chromatography (HPLC) retention time of about 10-15 minutes, more specifically about 12 minutes and even more specifically about 12.69 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm. In a particular embodiment, compound "D" may be characterized as deoxyviolacein (3), a known compound isolated earlier from *Chromobacterium violaceum*.

In another specific embodiment, the compound may have the following structure

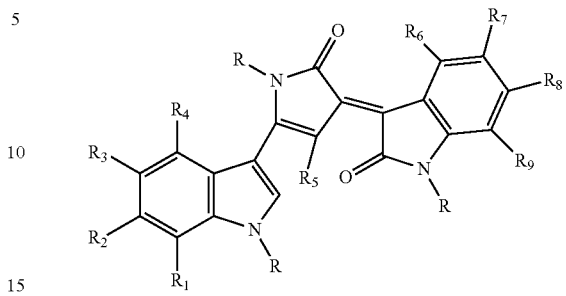

wherein R is —H, lower chain alkyl containing 1, 2, 3, 4, 5, 6, 7, 8 or 9 alkyl moieties, aryl or aryl alkyl moiety, substituted lower alkyl, halogens; $R_1$, $R_2$, $R_3$, $R_4$, $R_5$, $R_6$, $R_7$, $R_8$, $R_9$ are each independently H, are the same or different, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

Further provided is a method for (1) modulating pest (e.g., nematode, insect, soil-borne bacteria) infestation in a plant comprising applying to the plant and/or seeds thereof and/or substrate used for growing said plant or a method for modulating soil borne bacteria in soil comprising applying to the plant, seeds, and/or substrate an amount of (I) A Compound that
(a) has pesticidal and/or antimicrobial activity;
(b) has a molecular weight of about 950-1450 as determined by LTQ Orbitrap XL hybrid Fourier Transform Mass Spectrometer.
(c) has $^1H$ NMR δ values of 5.22 (sext, 1H), 2.62 (dd, 1H), 2.53 (dd, 1H), and 1.31 (d, 3H) (d) has $^{13}C$ NMR δ values of 169.2, 67.6, 40.9, and 19.8.
(d) comprises the structure —(—O—$CHCH_3$—$CH_2$—CO—)$_n$—, where n=6-50
(e) is obtainable from a *Chromobacterium* species and
(II) Optionally Another Pesticidal Substance effective to modulate infestation in said plant.

Compound (I) may have the structure:

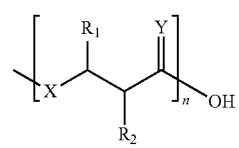

Wherein
X, is independently —O, —NR, or —S, wherein R is H or $C_1$-$C_{10}$ alkyl; Y, is independently —O, —S; n=6-50; $R_1$, $R_2$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In particular, the compound (I) has the structure:

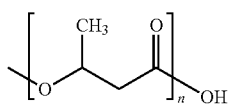

wherein n=10-25.

In a most specific embodiment, (I) is an alpha-butyric acid.

Further provided is a method for obtaining the compounds set forth above. The method comprises culturing a strain of a *Chromobacterium* sp. in a whole cell broth under conditions sufficient to produce the compound and isolating the compound produced from the whole cell broth.

In a related aspect, disclosed are methods for stabilizing biological pesticide compositions against physical separation and loss of activity due to exposure to sunlight by applying an amount of a stabilizing agent to said biological pesticide composition effective to stabilize the biological pesticide composition against physical separation and loss of activity due to exposure to sunlight. Also provided are compositions comprising such agents. In a particular embodiment, the pesticidal composition comprises *Chromobacterium* sp. filtrate, supernatant, extract or pesticidally active substance derived therefrom which may be present in the amount of at least about 0.5% and particularly between about 0.5 wt % based on dry cell weight to about 30 wt. %. The stabilizing agent may in a particular embodiment be a benzoic acid salt and/or lignin salt, particularly lignin sulfonate salt, including but not limited to sodium, potassium, calcium, magnesium, ammonium, and combinations thereof and may present in the amount of at least about 2.5 wt % and may preferably be present in the amount of about 5%-15%.

BRIEF DESCRIPTION OF THE FIGURES

FIG. 1 is a schematic representation of purification scheme for obtaining chromamide A (1) violacein (2) and deoxyviolacein (3). from culture broth.

FIG. 2 depicts chemical structures for chromamide A (1) violacein (2) and deoxyviolacein (3).

FIG. 3 shows results from MBI-203 TSSM Leaf disk assays. CFD represents Cells Freeze Dried, which were then reconstituted in water to represent a ½×, 1× and 2.5× dose of the original Whole Cell Broth.

FIG. 4 shows the mean number of eggs laid by potato psyllid females exposed to MBI-203 treated pepper leaf.

FIG. 5 shows the mean number of eggs oviposited by psyllid females 5 days post exposure to MBI-203 treated and untreated pepper leaf discs.

FIG. 6 shows the mean number of Green Peach Aphid (GPA) nymphs and adults on treated pepper leaf discs 24 hours post exposure of adults ($P<0.0001$, LSD, $\alpha=0.05$). Means of the same letter not statistically different from each other. $dH_2O$—negative control, 203 10% v/v—positive control.

FIG. 7 shows the mean number of Green Peach Aphid progeny (nymphs) on MBI-203 treated pepper leaf discs 3 days post exposure of adults ($P<0.0001$, LSD, $\alpha=0.05$). Means of the same letter not statistically different from each other. $dH_2O$—negative control, Avid 10% v/v—positive control.

FIG. 8 shows the mean number of Green Peach Aphid progeny (nymphs) on MBI-203 and DF2 (MBI-203 formulated product) treated pepper leaf discs 3 days post exposure of adults ($P<0.0001$, LSD, $\alpha=0.05$). Means of the same letter not statistically different from each other. $dH_2O$—negative control, Avid 10% v/v—positive control.

FIG. 9 is a schematic representation of purification scheme for violacein (2) and oligo-(β-hydroxybutyric acid (4). from culture broth.

FIG. 10 depicts the results of nematocidal bioassays of various fractions and of compound oligo-hydroxybutyric acid (1).

FIGS. 11A and 11B show the mean number of green peach aphid, *Myzus persicae* (nymphs and adults) on treated pepper leaf discs 24 hours post exposure. Means of the same letter are not significantly different from each other (LSD, $P<0.0001$, $\alpha=0.05$). 203 Me—MBI-203 crude extract in methanol solvent, Me—Methanol (blank treatment), 203, Ace—MBI-203 crude extract in acetone solvent, Ace—Acetone (blank treatment), $dH_2O$—negative control, Avid 10%—positive control.

FIGS. 12A and 12B show the mean number of green peach aphid, *Myzus persicae* (nymphs and adults) on treated pepper leaf discs 24 hours post exposure. Means of the same letter are not statistically different from each other. Ace—acetone only (blank treatment, DCM-, EA-, Wash-, MeOH—, $dH_2O$—negative control, 203 10%—MBI-203 std (positive control).

FIG. 13 shows the mean number of Green Peach Aphid progeny (nymphs) on treated pepper leaf discs 3 days post exposure of adults ($P<0.0018$, LSD, $\alpha=0.05$). Means of the same letter not statistically different from each other. VL1—violacein at 0.5 μg/mL, VL2—violacein at 1.0 μg/mL, Acetone—blank treatment, $dH_2O$—negative control, Avid 10% v/v—positive control.

FIG. 14 shows the mean number of Green Peach Aphid (GPA) nymphs and adults on treated pepper leaf discs 24 hours post exposure of adults ($P<0.0001$, LSD, $\alpha=0.05$). Means of the same letter not statistically different from each other. $dH_2O$—negative control, 203 10% v/v—positive control.

FIG. 15 shows the mean number of Green Peach Aphid (GPA) nymphs and adults on treated pepper leaf discs 24 hours post exposure of adults ($P<0.0001$, LSD, $\alpha=0.05$). Means of the same letter not statistically different from each other. $dH_2O$—negative control, 203 10% v/v—positive control.

FIG. 16 shows MBI-203 @ 3% presun vs postsun mortality, zeroed to water.

FIG. 17 shows MBI-203: Cabbage Aphid plant spray EP/EP+NaBenz.

FIG. 18 shows MBI-203 EP+/−Na Benz, Cabbage Aphids plant spray, corrected.

FIG. 19 shows MBI-203: EP+CaCO3/NaBenz PRE/POST SUN, normalized to negative control.

FIG. 20 shows MBI-203 EP SDP post sun, 3 and 6 day assays.

FIG. 21 shows MBI-203 EP w/ Na Benz+lignin in sun, assay day 4, corrected.

FIG. 22 shows MBI-203 EP w/ Na Benz+lignin in sun, percent activity loss, assay day 4.

FIG. 23 shows MBI-203: EP+lignin+sun, Broccoli CL assay day 3.

DETAILED DESCRIPTION OF THE PREFERRED EMBODIMENTS

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source.

A "carrier" as defined herein is an inert, organic or inorganic material, with which the active ingredient is mixed or formulated to facilitate its application to plant or other object to be treated, or its storage, transport and/or handling.

The term "modulate" as defined herein is used to mean to alter the amount of pest infestation or rate of spread of pest infestation.

The term "pest infestation" as defined herein, is the presence of a pest in an amount that causes a harmful effect including a disease or infection in a host population or emergence of an undesired weed in a growth system.

A "pesticide" as defined herein, is a substance derived from a biological product or chemical substance that increase mortality or inhibit the growth rate of plant pests and includes but is not limited to nematocides, insecticides, herbicides, plant fungicides, plant bactericides, and plant viricides.

A "biological pesticide" as defined herein is a microorganism with pesticidal properties.

Methods of Production

As noted above, the biological pesticide may comprise or be derived from an organism having the identifying characteristics of a *Chromobacterium* species, more particularly, from an organism having the identifying characteristics of a strain of *Chromobacterium substugae*, more particularly from a strain of *Chromobacterium substugae* sp. nov. which may have the identifying characteristics of NRRL B-30655, or alternatively from any other microorganism. The methods comprise cultivating these organisms and obtaining the compounds and/or compositions of the present invention by isolating these compounds from the culture of these organisms.

In particular, the organisms are cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media are available may be available from commercial sources or prepared according to published compositions.

After cultivation, the compounds and/or compositions of the present invention may be extracted from the culture broth. The extract may be fractionated by chromatography.

Compositions

The substances set forth above used in the compositions and methods disclosed herein can be formulated in any manner. Non-limiting formulation examples include but are not limited to Emulsifiable concentrates (EC), Wettable powders (WP), soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), etc. In any formulation described herein, percent of the active ingredient is within a range of 0.01% to 99.99%.

The compositions may be in the form of a liquid, gel or solid. Liquid compositions comprise pesticidal compounds derived from a *Chromobacterium* strain, e.g. a strain having the identifying characteristics of *Chromobacterium substugae* sp. Nov and more particularly, having the identifying characteristics of NRRL B-30655 (see U.S. Pat. No. 7,244,607).

A solid composition can be prepared by suspending a solid carrier in a solution of pesticidal compounds and drying the suspension under mild conditions, such as evaporation at room temperature or vacuum evaporation at 65° C. or lower.

A composition may comprise gel-encapsulated compounds derived from the *Chromobacterium* strain. Such gel-encapsulated materials can be prepared by mixing a gel-forming agent (e.g., gelatin, cellulose, or lignin) with a culture or suspension of live or inactivated *Chromobacterium*, or a cell-free filtrate or cell fraction of a *Chromobacterium* culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA Inerts List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition as set forth above also comprises a stabilizing agent, which stabilizes a biological pesticide composition against physical separation and loss of activity due to exposure to sunlight. This stabilizing agent may be a benzoic acid salt or lignin sulfonate salt.

The composition set forth above may be combined with another microorganism and/or pesticide (e.g, nematocide, fungicide, insecticide, antibiotic or anti-microbial agent). The microorganism may include but is not limited to an agent derived from *Bacillus* sp., *Pseudomonas* sp., *Brevabacillus* sp., *Lecanicillium* sp., non-*Ampelomyces* sp., *Pseudozyma* sp., *Streptomyces* sp, *Burkholderia* sp, *Trichoderma* sp, *Gliocladium* sp. Alternatively, the agent may be a natural oil or oil-product having fungicidal and/or insecticidal activity (e.g., paraffinic oil, tea tree oil, lemongrass oil, clove oil, cinnamon oil, citrus oil, rosemary oil). Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a Reynoutria extract.

The fungicide can also be a multi-site non-inorganic, chemical fungicide selected from the group consisting of chloronitrile, quinoxaline, sulphamide, phosphonate, phosphite, dithiocarbamate, chloralkythios, phenylpyridin-amine, cyano-acetamide oxime.

The composition may as noted above, further comprise an insecticide. The insecticide may include but is not limited to avermectin, Bt, neem oil, spinosads, *Burkholderdia* sp. as set forth in US Patent Appln. Pub. No. 2011-0207604, entomopathogenic fungi such a *Beauveria bassiana* and chemical insecticides including but not limited to organochlorine compounds, organophosphorous compounds, carbamates, pyrethroids, and neonicotinoids.

As noted above, the composition may further comprise a nematocide. This nematocide may include but is not limited to avermectin, microbial products such as Biome (*Bacillus firmus*), *Pasteuria* spp and organic products such as saponins Uses The compositions, cultures and supernatants and pesticidal compounds set forth above may be used as pesticides. In particular, the compounds or compositions as set forth above may be used as insecticides, bactericides (against soil-borne bacteria) and nematocides. Specifically, nematodes that may be controlled using the method set forth above include but are not limited to parasitic nematodes such as root-knot, cyst, and lesion nematodes, including but not limited to *Meloidogyne* sp. *Tylenchorhynchus* sp, *Hoplolaimus* sp., *Helicotylenchus* sp., *Pratylenchus* sp., *Heterodera* sp., *Globodera*, sp., *Trichodorus* sp. *Paratrichodorus* sp., *Xiphinema* sp., and *Criconema* sp.; particularly *Meloidogyne incognita* (root knot nematodes), as well as *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

As noted above, the active ingredient(s) and compositions set forth above may also be applied to locations containing Acari (arachnids), such as mites, including but not limited to, *Panonychus* sp. such as *Panonychus citri* (citrus red mite), and *Panonychus ulmi* (red spider mite), *Tetranychus* sp. such as *Tetranychus kanzawi* (Kanzawa spider mite), *Tetranychus urticae* (2 spotted spider mite), *Tetranychus pacificus* (Pacific spider mite), *Tetranychus turkestanii* (Strawberry mite) and *Tetranychus cinnabarinus* (Carmine spider mite), *Oligonychus* sp. such as *Oligonychus panicae* (avacado brown mite), *Oligonychus perseae* (persea mite), *Oligonychus pratensis* (Banks grass mite) and *Oligonychus coffeae*, *Aculus* sp. such as *Aculus cornatus* (Peach silver mite), *Aculus fockeni* (plum rust mite) and *Aculus lycopersici* (tomato russet mite), *Eotetranychus* sp. such as *Eotetranychus wilametti, Eotetranychus yumensis* (yuma spider mite) and *Eotetranychus sexmaculatis* (6-spotted mite), *Bryobia rubrioculus* (brown mite), *Epitrimerus pyri* (pear rust mite), *Phytoptus pyri* (Pear leaf blister mite), *Acalitis essigi* (red berry mite), *Polyphagotarsonemus latus* (Broad mite), *Eriophyes sheldoni* (citrus bud mite), *Brevipalpus lewisi* (citrus flat mite), *Phylocoptruta oleivora* (citrus rust mite), *Petrobia lateens* (Brown wheat mite), *Oxyenus maxwelli* (olive mite), *Rhizoglyphus* spp., *Tyrophagus* spp., *Diptacus gigantorhyncus* (bigheaded plum mite) and *Penthaleaa major* (winter grain mite), Avocado red mite, Flat mite, black and red Mango spider mite, Papaya leaf edgeroller mite, Texas citrus mite, European red mite, Grape erineum mite (blister mite), Pacific spider mite, Willamette spider mite; Pink citrus rust mite. Such locations may include but are not limited to crops that are infested with such mites or other arachnids (e.g., aphenids). Such locations may include but are not limited to crops that are infested with such mites or other arachnids (e.g., aphenids).

Phytopathogenic insects controlled by the method set forth above include but are not limited to non-Culicidae larvae insects from the order (a) Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; (b) Coleoptera, for example, *Agriotes* spp., *Alphitobius* sp., *Anomola* spp., e.g., *Anomala orientalis; Anthonomus* spp., *Atomaria linearis, Chaetocnema tibialis, Cosmopolites* spp., *Curculio* spp., *Cyclocephala* spp., e.g., *Cyclocephala lurida, Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Otiorhynchus sulcatus, Phlyctinus* spp., *Popillia* spp., e.g., *Popilla japonica, Psylliodes* spp., *Rhizopertha* spp-, eg., *Rhizotrogus majalis, Sitophilus* spp., *Sitotroga* spp., *Tenebrio* spp., *Tribolium* spp. and *Trogoderma* spp.; (c) Orthoptera, for example, *Blatta* spp., *Blattella* spp., *Gryllotalpa* spp., *Leucophaea maderae, Locusta* spp., *Periplaneta* spp. and *Schistocerca* spp.; (d) Isoptera, for example, *Reticulitermes* spp.; (e) Psocoptera, for example, *Liposcelis* spp.; (f) Anoplura, for example, *Haematopinus* spp., *Linognathus* spp., *Pediculus* spp., *Pemphigus* spp. and *Phylloxera* spp.; (g) Mallophaga, for example, *Damalinea* spp. and *Trichodectes* spp.; (h) Thysanoptera, for example, *Frankliniella* spp., *Hercinotnrips* spp., *Taeniothrips* spp., *Thrips palmi, Thrips tabaci* and *Scirtothrips aurantii*; (i) Heteroptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Tniatoma* spp.; (j) Homoptera, for example, *Aleurothrixus floccosus, Aleyrodes brassicae, Aonidiella spp., Aphididae, Aphis spp., Aspidiotus spp., Bactericera spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Triozidae spp., Trioza erytreae and Unaspis citri; (k) Hymenoptera, for example, Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.; (l) Diptera, for example, Aedes spp., Antherigona soccata, Bibio hortulanus, Calliphora erythrocephala, Ceratitis spp., Chrysomyia spp., Cuterebra spp., Dacus spp., Delia spp., Delia radicum, Drosophila spp., e.g., Drosophila suzukii; Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp. and Tipula spp.; (m) Siphonaptera, for example, Ceratophyllus spp. and Xenopsylla cheopis; (n) from the order Thysanura, for example, Lepisma saccharina; (o) Hemiptera, for example, Bactericera sp., e.g., Bactericera cockerelli.

The active ingredients may be applied to locations containing Scarabaeidae pests. These include but are not limited to soil, grass and various ornamental plants, trees and vegetables.

The active ingredient(s) and compositions set forth above may also be applied to locations containing the a Muscidae pest. These include but are not limited to indoor environments, garbage, animals, fences, corrals, barns, milking parlors, farrowing pens etc. containing animals (cattle, pigs, sheep, horses etc.)

The active ingredient(s) and compositions set forth above may further be applied to locations containing the active ingredient(s) and compositions containing a Tenebrionidae pest. These include but are not limited to grains, poultry and poultry dwellings enclosures (fences, corrals, barns, milking parlors, farrowing pens etc.) containing animals (cattle, pigs, sheep, horses etc.)

EXAMPLES

The composition and methods set forth above will be further illustrated in the following, non-limiting Examples. The examples are illustrative of various embodiments only and do not limit the claimed invention regarding the materials, conditions, weight ratios, process parameters and the like recited herein.

Example 1

Extraction of Chromamide, Deoxyviolacein and Violacein from Chromobacterium substugae The following procedure is used for the purification of compounds extracted from the culture of Chromobacterium substugae:

The culture broth derived from the 10-L fermentation *C. substugae* in L-broth is extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone/methanol (50/50) after which the acetone/methanol is filtered and dried under vacuum using rotary evaporator to give the crude extract. The crude extract is then fractionated by using Sephadex LH 20 size exclusion chromatography ($CH_2Cl_2$/$CH_3OH$; 50/50) to give 7 fractions (FIG. 1). These fractions are then concentrated to dryness using rotary evaporator and the resulting dry residues are screened for biological activity using a feeding assay with Cabbage looper (*Trichoplusia ni*) or Beet armyworm (*Spodoptera exigua*). The active fractions are then subjected to reversed phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

Chromamide A (1) and compound B were obtained from Fraction 1 and 2 respectively, whereas violacein (2) & deoxyviolacein (3) were purified from Fraction 5 obtained from Sephadex LH 20 chromatography.

Purification of Compounds

Purification of chromamide A (1) was performed by using HPLC C-18 column (Phenomenex, Luna 10u C18(2) 100 A, 250×10), water:acetonitrile gradient solvent system (0-10 min, 80-75% aqueous $CH_3CN$; 10-45 min, 75-60% aqueous $CH_3CN$; 45-55 min, 60-50% aqueous $CH_3CN$; 55-65 min, 50-100% aqueous $CH_3CN$; 65-70 min, 100% $CH_3CN$; 55-70 min, 0-80% aqueous $CH_3CN$) at 2.5 mL/min flow rate and UV detection of 210 nm. The active compound chromamide A (1), has retention time 23.19 min.

Purification of invention compound B was performed by using HPLC C-18 column (Phenomenex, Luna 10u C18 (2) 100 A, 250×10), water:acetonitrile gradient solvent system (0-10 min, 80-75% aqueous $CH_3CN$; 10-45 min, 75-60% aqueous $CH_3CN$; 45-55 min, 60-50% aqueous $CH_3CN$; 55-65 min, 50-100% aqueous $CH_3CN$; 65-70 min, 100% $CH_3CN$; 55-70 min, 0-80% aqueous $CH_3CN$) at 2.5 mL/min flow rate and UV detection of 210 nm, the active compound B, retention time 26.39 min.

Purification of violacein (2) and deoxyviolacein (3) was performed by using HPLC C-18 column (Phenomenex, Luna 10u C18(2) 100 A, 250×10), water:acetonitrile gradient solvent system (0-10 min, 70-60% aqueous $CH_3CN$; 10-40 min, 60-20% aqueous $CH_3CN$; 40-60 min, 20-0% aqueous $CH_3CN$; 60-65 min, 100% $CH_3CN$; 65-75 min, 0-70% aqueous $CH_3CN$) at 2.5 mL/min flow rate and UV detection of 210 nm, the active compounds violacein (2), had a retention time 7.86 min and deoxyviolacein (3) retention time 12.45 min.

Mass Spectroscopy Analysis of Compounds

Mass spectroscopy analysis of active peaks is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5μ 100 A column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 μL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The chromamide A (1) has a molecular mass of 860 in positive ionization mode. The LC-MS chromatogram for another active compound B suggests a molecular mass of 874 in positive ionization mode. Violacein (2) and deoxyviolacein (3) had the molecular masses of 313 and 327 respectively in positive ionization mode.

NMR Spectroscopy Analysis of Compounds

NMR-NMR spectra were measured on a Bruker 600 MHz gradient field spectrometer. The reference is set on the internal standard tetramethylsilane (TMS, 0.00 ppm). The amino acid analyses were carried out on Hitachi 8800 amino acid analyzer.

For structure elucidation, the purified chromamide A with molecular weight 860 is further analyzed using a 600 MHz NMR instrument, and has $^1$H NMR δ values at 8.89, 8.44, 8.24, 8.23, 7.96, 7.63, 6.66, 5.42, 5.36, 5.31, 5.10, 4.13, 4.07, 4.05, 3.96, 3.95, 3.88, 3.77, 3.73, 3.51, 3.44, 3.17, 2.40, 2.27, 2.11, 2.08, 2.03, 2.01, 1.97, 1.95, 1.90, 1.81, 1.68, 1.63, 1.57, 1.53, 1.48, 1.43, 1.35, 1.24, 1.07, 1.02, 0.96, 0.89, 0.88, 0.87, 0.80 (see FIG. 4) and has $^{13}$C NMR values of 173.62, 172.92, 172.25, 172.17, 171.66, 171.28, 170.45, 132.13, 130.04, 129.98, 129.69, 129.48, 125.48, 98.05, 70.11, 69.75, 68.30, 68.25, 64.34, 60.94, 54.54, 52.82, 49.72, 48.57, 45.68, 40.38, 39.90, 38.18, 36.60, 31.98, 31.62, 31.58, 29.53, 28.83, 27.78, 24.41, 23.06, 22.09, 20.56, 19.31, 18.78, 17.66, 15.80. The chromamide A was isolated as a white solid, which analyzed for the molecular formula $C_{43}H_{68}N_6O_{12}$ (13 degrees of unsaturation), by ESI high-resolution mass spectrometry (obsd M+m/z 861.5376, calcd M$^+$ m/z 861.5343). The $^1$H NMR spectral data of chromamide A in DMSO-d$_6$ exhibited 68 proton signals, in which nine protons [δ$_H$: 8.89, 8.44, 8.23, 8.22, 7.96, 7.64, 6.65, 5.10, 4.13], were assigned as either NH or OH due to lack of carbon correlation in a heteronuclear correlation NMR (HMQC) analysis. The $^{13}$C NMR spectrum, showed seven carbonyl signals [δ$_C$: 173.62, 172.92, 172.25, 172.17, 171.66, 171.28, 170.45] and in the $^1$H NMR spectrum, six characteristic α-amino protons signals [δ$_H$: 4.07, 4.06, 3.96, 3.95, 3.88, 3.72] were observed which demonstrate that chromamide A is a peptide.

Interpretation of 2D NMR data led to the assignment of three amino acid units of the six, one leucine (Leu), one valine (Val) and one glutamine (Gln). The presence of these amino acids were confirmed by results of amino acid analysis, which also showed the presence of the above three amino acids. Further analysis of DEPT and 2D NMR spectral data (COSY, HSQC and HMBC) established the presence three sub-structures I, II and III as showed below.

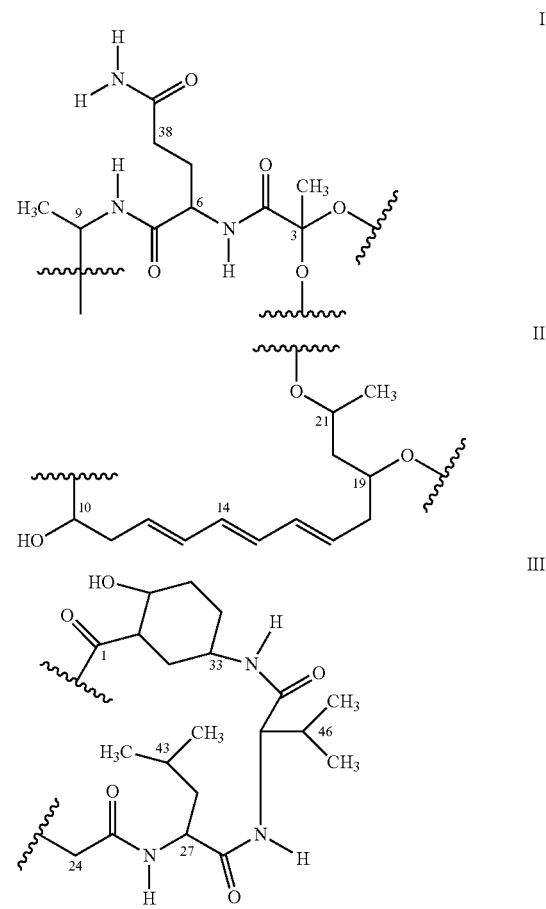

The connections of the three sub-structures in 1 were accomplished by routine HMBC NMR analysis using correlations between the α-amino proton and/or the secondary amide proton and the carbonyl carbon resonances and chemical shift consideration. The linkage of C-9 from sub-structure I to C-10 from sub-structure II was established by HMBC correlations from $CH_3$-40 [δ$_H$: 1.00] and the α-amino proton of alanine [δ$_H$: 3.42] to the C-10 carbon [δ$_C$: 70.11]. This was further confirmed by the three bond HMBC correlation from hydroxyl at [δ$_H$: 5.10] to C-9 at [δ$_C$: 49.78]. The methylene at [δ$_H$: 3.50] from sub-structure III showed a three bond HMBC correlation to C-19 [δ$_C$: 68.31] which connected the sub-structure I and II. The quaternary carbon at C-3 [δ$_C$: 98.09] was connected to C-21 [δ$_C$: 64.40] through a weak correlation from H-21 [δ$_H$: 3.95] together with their chemical shift values to form a one ring system. Lastly, the ring closure linkage was secured by a three-bond HMBC correlation from $H_3$-36 [δ$_H$: 1.43] to C-1 [δ$_C$: 172.17], which allowed the planar structure of chromamide A (1) to be assigned.

The compound B with a molecular weight 874 exhibited similar NMR and UV data suggesting that this compound B also belongs to the class of peptide.

Figure 2:
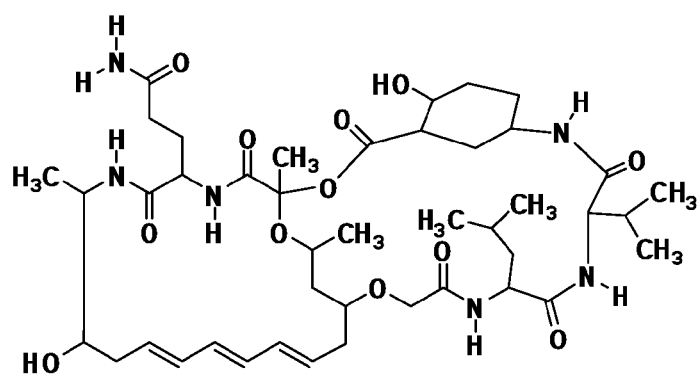
Figure 2:
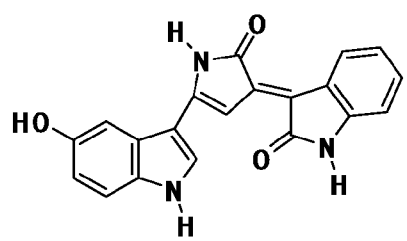
Figure 2:
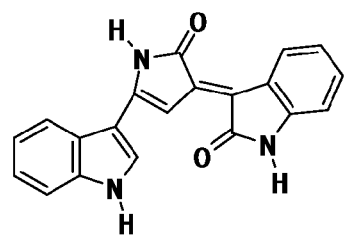
Figure 3:
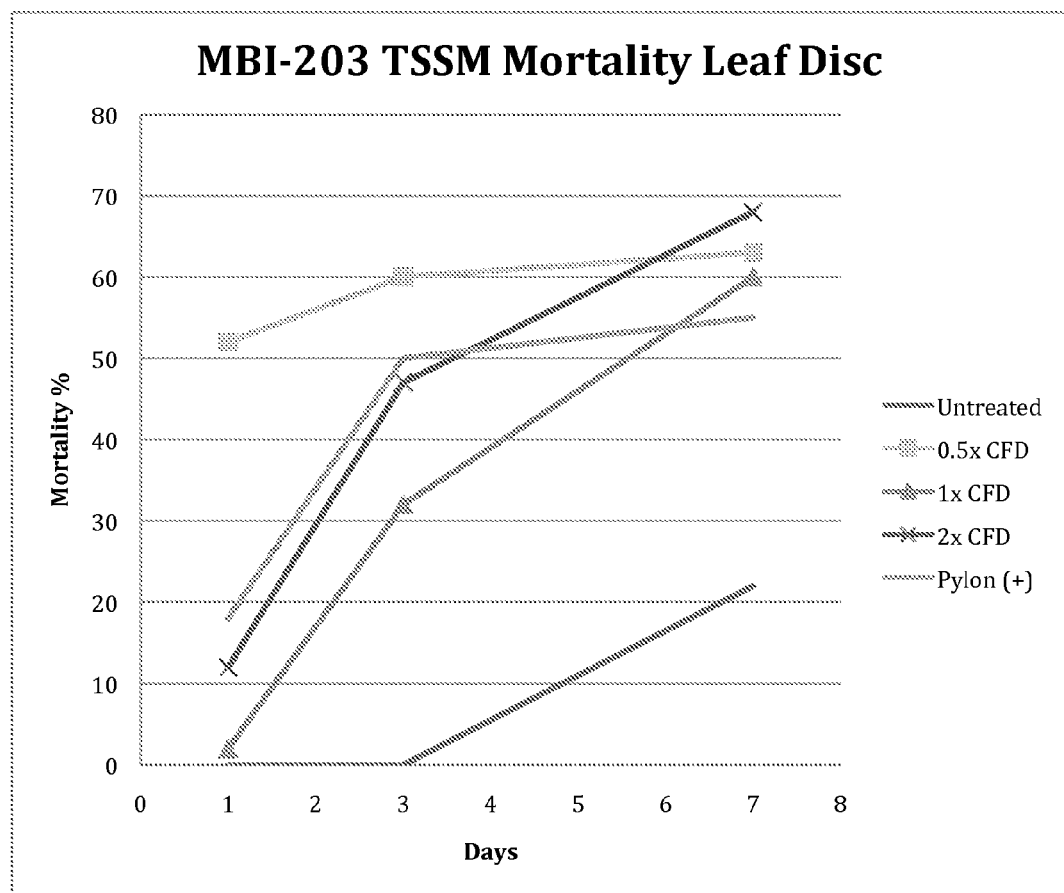

The structure for violacein (2) and deoxyviolacein (3) was assigned by comparison of the data of these compounds with those published in the literature. The structures of chromamide A, violacein and deoxyviolacein are shown in FIG. 2.

Example 2

Amino Acids Analysis of Chromamide A

Chromamide A (0.05 mg) was hydrolyzed by using liquid phase hydrolysis (6N HCL, 1% Phenol, 110° C., 24 hr, in vacuum). After cooling, the reaction mixture was dried and the hydrolyzed product was dissolved in Norleu dilution buffer to 1.0 mL volume. A 50 µl of the sample was loaded onto the ion-exchange column for analysis.

For standards and calibration, an amino acid standards solution for protein hydrolysate on the Na-based Hitachi 8800 (Sigma, A-9906) is used to determine response factors, and thus calibrate the Hitachi 8800 analyzer for all of the amino acids. Each injection contains NorLeucine as an internal standard to allow correction of the results for variations in sample volume and chromatography variables. System utilizes Pickering Na buffers, Pierce Sequanal grade HCl (hydrolysis), a Transgenomic Ion-Exchange column and an optimized method developed by Molecular Structure Facility (MSF), UC Davis, and the individual amino acid present in the sample are reported. The amino acids present in the sample (chromamide A) were found to be Glx (Glutamine/Glutamic acid), leu (leucine) and Val (Valine).

Example 3

Effect of *Chromobacterium substugae* (MBI-203) Against Two Spotted Spider Mites-Bean Plants Freeze dried MBI-203 was mixed with distilled water to varying concentrations of whole cell broth cell equivalent. Uninfested bean plants, *Phaseolus vulgaris*, were sprayed with MBI-203. Leaf disks were then taken from sprayed plants and placed in a petri dish as a food source for Two-Spotted Spider Mites, *Tetranychus urticae.* 10 mites were placed in each dish and incubated at 75° F., 12:12 (L:D). Evaluations of live and dead mites were recorded 1, 3, and 7 days after infestation. 1×CFD is freeze dried material reconstituted to whole cell broth cell concentrations (0.0103 g freeze dried/mL $dH_2O$). The results are shown in FIG. 3.

Example 4

Effect of *Chromobacterium substugae* (MBI-203) Against Two Spotted Spider Mites-Marigolds Marigolds, *Tagetes erecta*, were infested with Two-Spotted Spider Mites, *Tetranychus urticae*. Formulated product (MBI-203) or *Chenopodium ambrosioides* (marketed as REQUIEM® by AgraQuest, Inc., Davis, Calif.) was applied to infested plant and kept in a greenhouse with temperature ranges approximately 72-85° F. To sample, a 6 $cm^2$ leaf surface was harvested and number of live and dead nymphs and immature counted. The results are shown in Table 1.

TABLE 1

Comparison of MBI-203 with REQUIEM ®

| Treatment | Stage | Day 0 Live | Day 3 Live | Day 5 Live | Day 7 Live | Day 14 Live |
|---|---|---|---|---|---|---|
| Untreated | nymph | 155 | 165 | 180 | 181 | 200 |
| MBI-203 @ 1% | nymph | 146 | 74 | 144 | 218 | 216 |
| MBI-203 @ 5% | nymph | 142 | 92.8 | 143 | 170 | 175 |
| REQUIEM ® (+) | nymph | 142 | 145 | 147 | 158 | 153 |
| Untreated | Adult | 48 | 60.8 | 75.3 | 77 | 115 |
| MBI-203 @ 1% | Adult | 61.3 | 84.3 | 94 | 88.8 | 105 |
| MBI-203 @ 5% | Adult | 35.5 | 72.3 | 93.8 | 113 | 111 |
| REQUIEM ® (+) | Adult | 36.5 | 44 | 68 | 94.5 | 91.5 |

Example 5

Effect of *Chromobacterium substugae* (MBI-203) Screening Against Two Spotted Spider Mites (TSSM)-French Beans French beans infested with TSSM or abamectin-resistant TSSM were sprayed with 0.5%, 1%, 2%, and 4% v/v dilutions of formulated MBI-203 at approximately 100 gal/acre. Mortality was assessed 9 days after application. The results are shown in Table 2.

TABLE 2

Effect of MBI-203 on TSSM infestation in French Beans

| | Susceptible TSSM Reduction % | | | Abamectin-resistant TSSM Reduction % | | |
|---|---|---|---|---|---|---|
| Concentration | Eggs | Nymphs | Adults | Eggs | Nymphs | Adults |
| 0.5% | 0 | 0 | 0 | n/a | n/a | n/a |
| 1% | 0 | 0 | 0 | 0 | 0 | 0 |
| 2% | 8 | 15 | 25 | 0 | 0 | 0 |
| 4% | 55 | 55 | 60 | 0 | 0 | 0 |

Example 6

Screening MBI-203 Against Two Spotted Spider Mites in Strawberry

The efficacy of five traditional compounds and MBI-203 ingredients were evaluated for TSSM control on field strawberry transplants at the Florida Gulf Coast Research and Education Center. Seedlings were transplanted in the field (day 0). Each 12.5-ft. plot consisted of 20 plants. Plots were infested four times from day 55 through day 71 with 10 to 20 motile TSSM per plant. Seventeen treatments of various rates and schedules of application of miticides, some combined with an adjuvant, and a non-treated check were replicated four times in a RCB design. Treatments were applied using a hand-held sprayer with a spray wand outfitted with a nozzle containing a 45-degree core and a number four disc. The sprayer was pressurized by $CO_2$, to 40 psi, and calibrated to deliver 100 gal per acre. Samples were collected weekly from day 90 before first spray through 2 wks after the last application of treatments (day 154). Samples consisted of ten randomly selected leaflets per plot and were collected from the middle one-third stratum of the plants. Motile and egg TSSM were brushed from the leaflets onto rotating sticky discs and counted. No phytotoxicity was observed. Results are shown in Tables 3 and 4.

TABLE 3

The efficacy of five traditional chemistry-derived and two biologically-derived active ingredients for TSSM control

| Treatment/ Formulation[a] | Rate amt/ acre | Number of motile TSSM/leaflet | | | | | | | | | |
|---|---|---|---|---|---|---|---|---|---|---|---|
| | | day 90 | day 98 | day 105 | day 111 | day 118 | day 125 | day 132 | day 139 | day 146 | day 154 |
| Non-treated | — | 8.8 a | 2.0 a | 7.3 a | 4.8 a | 14.3 a | 47.5 a | 89.8 a | 150.5 a | 277.5 a | 319.0 a |
| Abamectin as a.i[d] (marketed as AGRI-MEK ® 0.15 EC, Syngenta Inc.) | 16 fl. oz. | 8.5 a | 4.5 a | 6.3 a | 5.3 a | 0.5 e | 0.5 h | 3.0 d-f | 6.3 fg | 6.8 g-i | 15.3 e-g |
| Bifenzate as a.i[d] (marketed as ACRAMITE ® 50WS, Chemtura) + INDUCE ®[b] | 1 lb. | 3.8 a | 6.0 a | 6.0 d | 0.8 c | 8.3 b-f | 20.5 c-e | 3.0 i | 28.0 ef | 66.5 de | 128.3 b-f |
| COHERE ®[c] | 16 fl. oz. | 2.8 a | 5.5 a | 7.0 a | 5.5 a | 14.3 ab | 34.3 ab | 72.5 ab | 121.3 ab | 237.8 a | 270.0 a |
| Spiromesifin as a.i[d] + INDUCE ®[b] | 12 fl. oz. | 2.8 a | 2.3 a | 2.0 a | 2.3 a | 0.5 e | 0.8 gh | 0.5 ef | 2.5 gh | 2.8 i | 6.0 g |
| Fenpyroximate as a.i[d] (marketed as PORTAL® 5% EC, Nichino America) | 32 fl. oz. | 4.5 a | 3.8 a | 6.5 a | 2.8 a | 2.0 c-e | 7.3 c-f | 5.3 de | 10.0 e-g | 34.3 d-f | 145.3 a-c |
| Hexythiazox as a.i[d] (marketed as SAVEY ® 50DF, Gowan) | 6 oz. | 2.0 a | 1.8 a | 2.8 a | 6.0 a | 13.8 ab | 23.0 ab | 57.5 ab | 103.3 ab | 196.0 ab | 285.5 a |
| MBI-203 + INDUCE ®[b] | 1 gal. | 4.3 a | — | 9.5 a | 7.8 a | 10.3 a-d | 18.0 a-d | 54.5 ab | 97.8 a-c | 196.3 ab | 218.0 ab |
| MBI-203 + INDUCE ®[b] | 3 gal. | 2.8 a | — | 4.5 a | 5.3 a | 16.0 ab | 8.8 b-e | 22.5 bc | 38.8 b-d | 87.5 b-d | 156.0 a-c |
| $F_{17,51}$ | | 1.35 | 0.75 ($F_{13,39}$) | 1.34 | 0.94 | 4.44 | 7.82 | 11.12 | 13.26 | 15.86 | 13.84 |
| P-value | | 0.20 | 0.70 | 0.21 | 0.53 | <0.0001 | <0.0001 | <0.0001 | <0.0001 | <0.0001 | <0.0001 |

Data were transformed $\log_{10}(x + 1)$ prior to ANOVA; non-transformed means are reported. Means within a column followed by the same letter are not significantly different by Fisher's Protected LSD (P ≤ 0.05).
[a]A '+' sign indicates the products were combined.
[b]INDUCE ®, (Aquatic Ecosystems, Inc.), non-ionic surfactant, applied at 32 fl. oz./acre.
[c]COHERE ® , (Helena Chemical Company), non-ionic spreader-sticker adjuvant, applied at 16 fl. oz./acre.
[d]a.i. is active ingredient

TABLE 4

The efficacy of five traditional chemistry-derived and two biologically-derived active ingredients for TSSM control

| Treatment/ Formulation[a] | Rate amt/acre | Number of eggs TSSM/leaflet | | | | | |
|---|---|---|---|---|---|---|---|
| | | day 90 | day 98 | day 105 | day 111 | day 118 | day 125 |
| Non-treated | — | 15.5 a | 10.0 a | 27.5 ab | 12.3 a | 25.3 a | 122.0 a |
| Abamectin as a.i[d] (marketed as AGRI-MEK ® 0.15 EC, Syngenta Inc.) | 16 fl. oz. | 6.8 a | 17.0 a | 26.5 ab | 12.0 ab | 1.3 ef | 2.3 gh |
| Bifenzate as a.i[d] (marketed as ACRAMITE ® 50WS, Chemtura) + INDUCE ® | 1 lb. | 3.8 a | 6.0 a | 6.0 d | 0.8 c | 8.3 b-f | 20.5 c-e |
| COHERE ® | 16 fl. oz. | 6.8 a | 15.5 a | 11.8 a-d | 16.8 a | 31.5 ab | 148.3 a |
| Spiromesifin as a.i[d] + INDUCE ®[b] | 12 fl. oz. | 7.3 a | 5.3 a | 7.3 d | 5.0 bc | 1.5 d-f | 2.3 f-h |
| Fenpyroximate as a.i[d] (marketed as PORTAL® 5% EC, Nichino America) | 32 fl. oz. | 9.3 a | 11.8 a | 12.3 cd | 12.5 ab | 1.0 f | 34.5 bc |

TABLE 4-continued

| | | | | | | | |
|---|---|---|---|---|---|---|---|
| Hexythiazox as a.i[d] (marketed as SAVEY ® 50DF, Gowan) | 6 oz. | 2.0 a | 8.5 a | 15.0 a-d | 17.0 a | 22.0 ab | 71.5 ab |
| MBI-203 + INDUCE ® | 1 gal. | 8.0 a | — | 27.3 ab | 20.5 a | 19.5 ab | 56.3 ab |
| MBI-203 + INDUCE ® | 3 gal. | 5.0 a | — | 11.0 b-d | 14.5 a | 11.0 a-c | 30.0 bc |
| $F_{17,51}$ | | 0.95 | 0.96 ($F_{13,39}$) | 2.12 | 1.93 | 4.48 | 13.52 |
| P-value | | 0.5194 | 0.5042 | 0.0201 | 0.0363 | <0.0001 | <0.0001 |

Number of eggs TSSM/leaflet

| Treatment/ Formulation[a] | day 132 | day 139 | day 146 | day 154 |
|---|---|---|---|---|
| Non-treated | 181.5 a | 587.0 a | 559.0 a | 423.0 a |
| Abamectin as a.i[d]. (marketed as AGRI-MEK ® 0.15 EC, Syngenta Inc.) | 6.5 hi | 3.5 f-h | 3.5 gh | 41.3 e-g |
| Bifenzate as a.i[d]. (marketed as ACRAMITE ® SOWS, Chemtura) + INDUCE ® | 3.0 i | 28.0 ef | 66.5 de | 128.3 b-f |
| COHERE ® | 114.0 ab | 321.0 ab | 525.3 a | 377.0 a |
| Spiromesifin as a.i[d] + INDUCE ®[b] | 2.8 hi | 0.8 h | 4.5 f-h | 25.5 fg |
| Fenpyroximate as a.i[d] (marketed as PORTAL® 5% EC, Nichino America) | 20.8 de | 28.5 d | 97.3 cd | 240.8 a-d |
| Hexythiazox as a.i[d] (marketed as SAVEY ® 50DF, Gowan) | 128.5 ab | 281.5 ab | 393.5 ab | 533.0 a |
| MBI-203 + INDUCE ® | 91.8 a-c | 187.3 bc | 304.5 | 432.3 a |
| MBI-203 + INDUCE ® | 35.5 c-e | 57.8 cd | 238.3 a-c | 341.5 ab |
| $F_{17,51}$ | 18.40 | 19.96 | 19.16 | 5.13 |
| P-value | <0.0001 | <0.0001 | <0.0001 | <0.0001 |

Data were transformed $\log_{10}(x+1)$ prior to ANOVA; non-transformed means are reported. Means within a column followed by the same letter are not significantly different by Fisher's Protected LSD ($P \leq 0.05$).
[a]A '+' sign indicates the products were combined.
[b]INDUCE ®, (Aquatic Ecosystems, Inc.), non-ionic surfactant, applied at 32 fl. oz./acre.
[c]COHERE ®, (Helena Chemical Company), non-ionic spreader-sticker adjuvant, applied at 16 fl. oz./acre.
[d]a.i. is active ingredient Example 7

Effect of *Chromobacterium substugae* (MBI-203) Against House Flies

Test substance is screened for direct contact efficacy against houseflies (adults). There are three treatment groups for each compound: 1.5%, 3% and 6% concentration plus an untreated control. Each group contains five replicates with approximately 10 insects each. Arthropods will be treated with a hand pump sprayer until "full coverage" is reached, in 16 oz. drink cups with a beverage lid. At four hours, a cotton ball with 10% sucrose solution is provided for the flies by inserting it into the perforation in the lid. Data is taken at 5, 15, 30, 45, 60 minutes and 2, 4, and 24 hours or until endpoint. Knockdown and mortality were determined by counting the relative number of prone insects. Moribund insects were not included in mortality totals. Results are shown below in Table 5.

Example 8

Effect of *Chromobacterium substugae* (MBI-203) Against Litter Beetles

Three treatment groups were tested for each compound: 1.5%, 3% and 6% concentration plus an untreated control. Each group contained five replicates with approximately 10 insects each. Arthropods were treated with a hand pump sprayer until "full coverage" was reached, in 8 or 16 oz deli squat cups with perforated lids with filter paper on the bottom to absorb any excess material. Knockdown and mortality were observed at 5, 15, 30, 45, 60 minutes and 2, 4, 24, 48, and 72 hours after treatment. Knockdown and mortality were determined by counting the relative number of prone insects. Moribund insects were not included in mortality totals. Results are shown below in Table 6.

TABLE 5

| | Rate | Knockdown | | | | | | | Mortality | | |
|---|---|---|---|---|---|---|---|---|---|---|---|
| | | 5 min | 15 min | 30 min | 45 min | 1 hr | 2 hr | 4 hr | 24 hr | 48 hr. | 72 hr |
| House Fly (ZCS) Musca domestica | 1.5% | 10.0% | 28.0% | 54.0% | 58.0% | 64.0% | 70.0% | 76.0% | 80.0% | 80.0% | 80.0% |
| | 3% | 14.9% | 36.2% | 59.6% | 74.5% | 80.9% | 80.9% | 80.9% | 85.1% | 89.4% | 95.7% |
| | 6% | 47.7% | 68.2% | 97.7% | 97.7% | 97.7% | 97.7% | 97.7% | 97.7% | 100.0% | 100.0% |

TABLE 6

| | Rate | Knockdown | | | | | | | Mortality | | |
|---|---|---|---|---|---|---|---|---|---|---|---|
| | | 5 min | 15 min | 30 min | 45 min | 1 hr | 2 hr | 4 hr | 24 hr | 48 hr. | 72 hr |
| Litter Beetle-larvae Alphitobius diaperinus | 3% | 33.3% | 47.9% | 50.0% | 58.3% | 68.8% | 75.0% | 77.1% | 85.4% | 93.8% | 85.4% |
| | 6% | 45.1% | 64.7% | 72.5% | 76.5% | 76.5% | 82.4% | 76.5% | 86.3% | 88.2% | 86.3% |
| | 1.5% | 40.0% | 58.0% | 62.0% | 64.0% | 74.0% | 78.0% | 78.0% | 72.0% | 90.0% | 86.0% |
| | 3% | 70.0% | 82.0% | 92.0% | 86.0% | 88.0% | 92.0% | 88.0% | 94.0% | 98.0% | 100.0% |
| | 6% | 84.3% | 96.1% | 98.0% | 98.0% | 100.0% | 100.0% | 100.0% | 98.0% | 100.0% | 96.1% |
| Litter Beetle-adult Alphitobius diaperinus | 1.5% | 0.0% | 12.0% | 20.0% | 22.0% | 34.0% | 42.0% | 50.0% | 68.0% | 70.0% | 70.0% |
| | 3% | 2.0% | 2.0% | 12.0% | 14.0% | 24.0% | 28.0% | 28.0% | 54.0% | 54.0% | 56.0% |
| | 6% | 0.0% | 8.0% | 12.0% | 22.0% | 36.0% | 40.0% | 40.0% | 76.0% | 80.0% | 78.0% |
| | 1.5% | 4.0% | 6.0% | 10.0% | 12.0% | 14.0% | 18.0% | 22.0% | 24.0% | 30.0% | 32.0% |
| | 3% | 6.0% | 24.0% | 28.0% | 32.0% | 42.0% | 64.0% | 72.0% | 94.0% | 94.0% | 94.0% |
| | 6% | 10.0% | 22.0% | 30.0% | 38.0% | 62.0% | 78.0% | 86.0% | 86.0% | 94.0% | 90.0% |

Example 9

Effect of MBI-203 on Egg Laying Capacity of Potato Psyllids, *Bactericera cockerelli* Methods The egg laying capacity of potato psyllid females exposed to MBI-203 treated pepper leaves were determined Pepper leaves were excised at the petiole and treated with MBI-203 by dipping for 1 minute. Treatments in the experiment were as follows: MBI-203 at 10% v/v in $dH_2O$, $dH_2O$ as negative control and Avid at 10% v/v as positive control. Treated leaves were held in plastic petri dishes with the rims welled off, lined with craft foam with the center diameter cut out to expose treated leaf.

Four, 1-day old females were placed in the center of the dish where the treated leaf was exposed (cut out portion of the craft foam), covered with the petri plate cover, and the setup was secured with 2 binder clips. The female adults were allowed to lay eggs and egg count was done 3 to 10 days post exposure.

A follow up leaf disc bioassay on MBI-203 treated and untreated leaves was conducted to verify the effect of MBI-203 on the egg laying capacity of potato psyllid females. Treatment of MBI-203 at 3% v/v in water and an untreated control, $dH_2O$ only (negative control) were used in the assay. Pepper leaf discs (from 3-4 week old pepper plants) were cut in circles using a 23 mm cookie cutter, selecting a flat portion of the leaf to make sure the disc can be evenly laid flat on the agar plate after treatment with the compound. The bottom of the plates was covered with 30 µL of 1% agar solution, just enough to cover the bottom of the plate to prop leaf discs and maintain humidity. The agar was allowed to solidify by cooling at room temperature. Treatment of leaf disc was performed by pouring the treatment solution into a glass petri dish. With the solution in the dish, leaf discs were treated by soaking, swirling the dish gently to completely soak and coat the leaf discs. Treatment was performed for 1 minute and treated leaf discs were then allowed to dry for 10-15 minutes in fume hood or until the solution had completely dried off. In each solidified agar plate, 20-30 µL $dH_2O$ was pipeted onto the agar. Each treated leaf disc was laid individually onto the agar plate, placing the leaf disc abaxial side down on wetted agar, pressed down gently to completely flatten the disc into the agar. In each plate with treated leaf disc (treatment), 4 female psyllids were introduced. The petri plates with gravid females were then covered with the petri plate cover, poked with tiny holes for aeration and to prevent condensation. The dishes were sealed with parafilm and kept at room temperature. The number of eggs laid was counted daily, starting a day post introduction of females. The experiment was done in 3 replications, repeated two times.

Results

Figure 4:
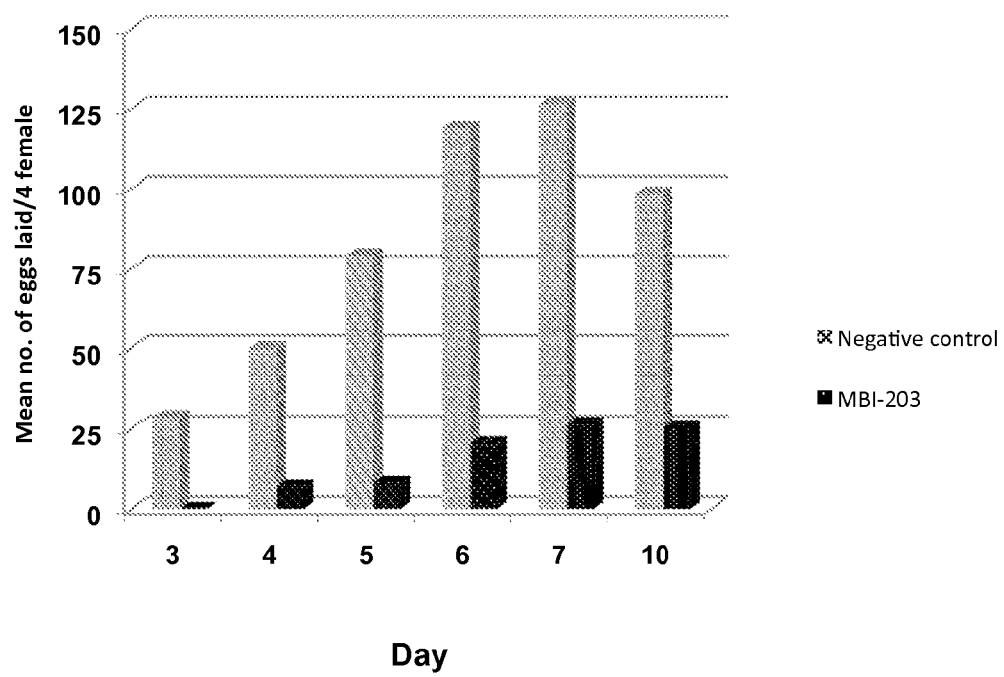

A significant reduction of eggs by females exposed to MBI-203 treatment was observed. A slight delay in egg oviposition was apparent on females in MBI-203 treated leaf discs. Psyllid females exposed to MBI-203 treated leaf discs started ovipositing eggs 3 days post exposure (FIG. 4). Eggs laid by females peaked on day 7 and declined at day 10. At day 10, mean egg count decreased as eggs laid by females started hatching. The females exposed to the positive control treatment (Avid 10% v/v) were all dead in day 3 with no eggs deposited on the avid treated leaf discs.

Figure 5:
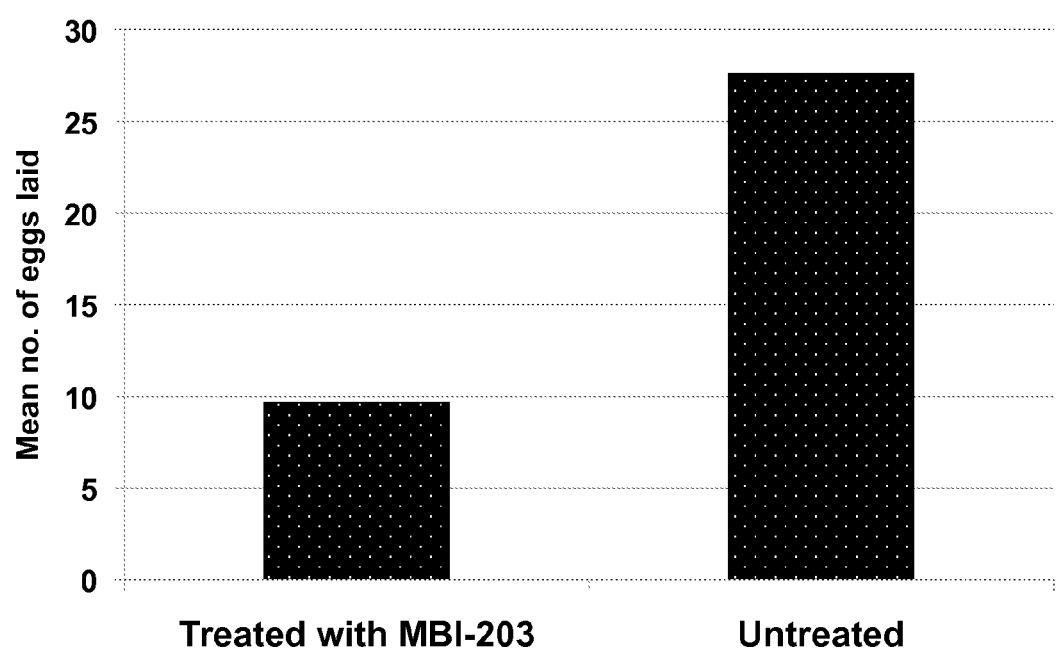

Verification leaf disc bioassays confirmed a consistent result with a significant reduction of eggs oviposited by females on MBI-203 treated leaf disc at 3% v/v (FIG. 5). A 65% egg reduction was exhibited by females exposed to MBI-203 treated leaf discs compared to females exposed to untreated leaf discs ($dH_2O$ only). These bioassay results indicate that MBI-203 affects the physiology of the psyllid females affecting their egg laying capacity.

Example 10

Effect of MBI-203 on Grubs and Scarabs

Control of White Grubs on Turf Grasses

Insecticides were evaluated for control of white grubs (Southern Masked Chafer, *Cyclocephala lurida* Bland) on a Kentucky bluegrass (*Poa pratensis* L.) and perennial ryegrass rough (*Lolium perenne* L.) at the North Bend golf course in North Bend, Nebr. Insecticides were applied to 5×5 ft plots arranged in a randomized complete block (RCB) design with 5 replications. Liquid products were applied using a $CO_2$ sprayer at 40 psi and applying 174 gpa finished spray. Within 24 h following application, all treatments were irrigated with 0.25 in of water. Formulations were evaluated 24 days and 48 days after treatment (DAT) by removing from each plot three, 8-inch diameter turf-soil cores (1.05 $ft^2$ total area) to a depth of 3 inches and counting the number of surviving and moribund grubs. Plots were periodically assessed for phytotoxicity. The results are shown in Tables 7 and 8.

There appears to be a correlation between application rate and percent control for the MBI-203 DF1 treatments. All treatments, except MBI-203 DF1 (2 fl oz/100 ft2), outperformed trichlorfon 6% (marketed as DYLOX® 420 SL (6.9 fl.oz/1000 $ft^2$) by Bayer CropScience, Inc., an industry standard insecticide for white grub control). Interestingly, moribund individuals were found in all treatments of MBI-203 AF1 and MBI-203 DF1. These numbers (in parenthesis) were not used in the statistical analysis but were included for comparative purposes. No phytotoxicity was observed. AF1 is an aqueous flowable and DF1 is a wettable powder formulation of *Chromobacterium substugae*.

TABLE 7

Efficacy MBI-203 in controlling White Grubs 24 days after Treatment (24 DAT)

| Treatment/ formulation | Rate fl oz/1000 $ft^2$ | Rep 1 | Rep 2 | Rep 3 | Rep 4 | Rep 5 | Mean WG ± SE 1.05 $ft^2$ | % Control |
|---|---|---|---|---|---|---|---|---|
| MBI-203 AF1 | 16 | 5 (2) | 4 (2) | 1 | 2 | 0 | 2.4 ± 0.9 | 76.0 |
| MBI-203 DF1 | 8 | 8 (1) | 4 (1) | 2 | 3 | 2 | 3.8 ± 1.1 | 62.0 |
| MBI-203 AF1 | 8 | 3 (3) | 9 (3) | 7 (1) | 5 (3) | 0 | 4.8 ± 1.6 | 52.0 |
| MBI-203 AF1 | 32 | 9 (3) | 5 | 7 | 4 | 0 | 5.0 ± 1.5 | 50.0 |
| MBI-203 DF1 | 4 | 5 | 6 (1) | 10 | 2 (1) | 2 (2) | 5.0 ± 3.2 | 50.0 |
| Dylox 420 SL | 6.9 | 0 | 6 | 9 | 9 | 4 | 5.6 ± 1.7 | 44.0 |
| MBI-203 DF1 | 2 | 2 (1) | 8 (2) | 8 | 9 | 6 | 6.6 ± 1.2 | 34.0 |
| UTC | — | 9 | 8 | 15 | 8 | 10 | 10.0 ± 1.3 | — |

TABLE 8

Efficacy MBI-203 in controlling White Grubs 24 days after Treatment (43 DAT)

| Treatment/ Formulation | Rate fl oz/ 1000 $ft^2$ | Rep 1 | Rep 2 | Rep 3 | Rep 4 | Mean WG 1.05 $ft^2$ | % Control |
|---|---|---|---|---|---|---|---|
| MBI-203 DF2 | 4.0 | 2 | 0 | 0 | 0 | 0.5 a | 95.0 |
| Dylox 6.2 G | 3 lb | 3 | 3 | 0 | 0 | 1.5 a | 85.0 |
| MBI-203 DF2 | 2.0 | 0 | 0 | 6 | 4 | 2.5 a | 75.0 |
| MBI-203 DF2 | 8.0 | 10 | 2 | 6 | 1 | 4.75 a | 52.5 |
| UTC | — | 15 | 8 | 10 | 7 | 10.0 b | — |

Means followed by the same letter are not significantly different (P > 0.05, LSD = 4.4).

Feeding Study of the Effect of MBI-203 on Other Root Feeding Scarabs

Unsterilized Groton soil, 4.25 pH, 14% organic matter was infested with the scarab, oriental beetle larvae (*Anomala orientalis*) and rated on the number of larvae that died. The soil was dosed with aqueous flowable formulation of MBI-203 and the percent mortality computed:

TABLE 9

Effect of MBI-203 on Oriental Beetle Larvae

|  | Trial 1 | Trial 2 |
|---|---|---|
|  | % mortality 7 DAT (days after treatment) | |
| 1.5 ml product/5 g soil (30% soil mixture) | 100 | 100 |
| 1 ml product/5 g soil (20% soil mixture) | 100 | 100 |
| .5 ml product + .5 ml de-ionized water/5 g soil | 87 | 100 |
| .25 ml product + .75 ml de-ionized water/5 g soil | 93 | 100 |
| .1 ml product + .9 ml de-ionized water/5 g soil | 40 | 13 |
| .05 ml product + .95 ml de-ionized water/5 g soil | 27 | 27 |
| Untreated Control (30% moisture) | 0 | 7 |
| Untreated Control (20% moisture) | 0 | 0 |

A similar trial was set up with the scarab, *Rhizotrogus majalis*, (European chafer) grubs using 1.5 ml and 1 ml product in 5 g soil. 100/100 larvae were killed at 7 DAT and none were killed in the Control.

Trials were also conducted with black vine weevil larvae *Otiorhynchus sulcatus* (Curculionidae) with potting media (no food source), carrots and *Taxus* roots. Results are shown in Tables 10, 11, 12 and 13.

TABLE 10

Effect of MBI-203 with Potting Soil

|  | % mortality 7 DAT | % mortality 14 DAT |
|---|---|---|
| .9 ml product/3 g media (30% soil moisture) | 0 | 0 |
| .6 ml product/3 g media (20% soil moisture) | 0 | 0 |
| Control (30% moisture) | 0 | 0 |
| Control (20% moisture) | 0 | 0 |

TABLE 11

Effect of MBI-203 with Carrots Dipped in Product

| | % mortality 3 DAT |
|---|---|
| Carrot slice dipped in product | 100 |
| Carrot slice dipped in de-ionized water (control) | 0 |

TABLE 12

Effect of MBI-203 with *Taxus* Roots

| | % mortality 3 DAT |
|---|---|
| *Taxus* roots dipped in product and dried | 90 |
| *Taxus* roots dipped in de-ionized water and dried | 0 |

TABLE 13

Effect of MBI-203 with Carrot Slice (Dried)

| | % mortality 3 DAT |
|---|---|
| Carrot slice dipped in product and dried | 60 |
| Carrot slice dipped in de-ionized water and dried (control) | 0 |

It appears that MBI-203 is very active against root feeding scarab beetles and weevil, particularly when fed a treated food source.

Example 11

Effect of MBI-203 Against Cabbage Root Maggot

This study was conducted to determine the efficacy of MBI-203 formulations for control of Cabbage Maggots (*Delia radicum*) on broccoli plants in a caged greenhouse study. Experimental treatments of MBI-203 DF-1 (a wettable powder formulation of MBI-203) at rates of 2 oz/1000 ft$^2$ and 8 oz/1000 ft$^2$; MBI-203 DF-2 (a second wettable powder formulation of MBI-203) at rates of 2 oz/1000 ft$^2$ and 8 oz/1000 ft$^2$. Experimental treatments were compared to the commercial standard, RADIANT® (marketed by DowAgro Sciences and containing spineforam as an active ingredient) at a rate of 1 lb/gal.

The number of live adult insects was recorded weekly up to 14 days after the third application (14DA-C) and the number of live larvae was recorded weekly up to 21 DA-C. Results showed that MBI 203 DF-1 had a significantly fewer number of adults emerge by the last evaluation date, and was comparable to RADIANT®. MBI-203 DF-1 had a significantly lower number of adults emerge than the UTC by the last evaluation date, and was comparable in control to Radiant.

TABLE 14

Maggot Count. Average number of larval *Delia radicum* insects per treatment, listed by evaluation date.

| Trt No. | Treatment Name | Rate | Rate Unit | Appl Code | 7 DA-C | 14 DA-C | 21 DA-C |
|---|---|---|---|---|---|---|---|
| 1 | Untreated | | | ABC | 5.75 a | 6.25 a | 6.50 a |
| 2 | MBI 203 DF-1 | 2 | oz/1000 ft$^2$ | ABC | 5.00 ab | 5.00 ab | 4.25 b |
| 3 | MBI 203 DF-1 | 8 | oz/1000 ft$^2$ | ABC | 4.75 ab | 3.00 c | 3.50 bc |
| 4 | MBI 203 DF-2 | 2 | oz/1000 ft$^2$ | ABC | 6.50 a | 5.50 ab | 4.25 b |
| 5 | MBI 203 DF-2 | 8 | oz/1000 ft$^2$ | ABC | 5.25 ab | 3.00 c | 1.50 cd |
| 8 | Radiant | 10 | fl oz/a | AC | 1.50 c | 1.00 d | 1.00 d |

TABLE 15

Percent Control. Average percent control of larval *Delia radicum* insects per treatment, listed by evaluation date.

| Trt No. | Treatment Name | Rate | Rate Unit | Appl Code | 7 DA-C | 14 DA-C | 21 DA-C |
|---|---|---|---|---|---|---|---|
| 1 | Untreated | | | ABC | 0.00 c | 0.00 d | 0.00 d |
| 2 | MBI 203 DF-1 | 2 | oz/1000 ft$^2$ | ABC | 13.04 bc | 20.00 cd | 34.62 c |
| 3 | MBI 203 DF-1 | 8 | oz/1000 ft$^2$ | ABC | 17.39 bc | 52.00 b | 46.15 bc |
| 4 | MBI 203 DF-2 | 2 | oz/1000 ft$^2$ | ABC | 0.00 c | 12.00 cd | 34.62 c |
| 5 | MBI 203 DF-2 | 8 | oz/1000 ft$^2$ | ABC | 8.70 bc | 52.00 b | 76.92 ab |
| 8 | Radiant | 10 | fl oz/a | AC | 73.91 a | 84.00 a | 84.62 a |

Example 12

Efficacy of MBI-203 DF1 and MBI-203 DF2 for the control of *Drosophila suzukii* (Spotted Wing *Drosophila* (SWD)) on Strawberry in the Greenhouse This study was conducted to determine the efficacy of MBI-203 DF1 and MBI-203 DF2 for the control of Spotted Winged *Drosophila* (SWD) on strawberry crops in the greenhouse. Experimental treatments of MBI-203 DF1 and MBI-203 DF2 were applied at rates of 1 lb/a and 4 lb/a to replicate plots. Treatments were compared to the commercial standard, Entrust® at a rate of 1.5 oz/a. All treatments were combined with the surfactant SILWET® L77 (Chemtura AgroSolutions, Inc.) at a rate of 0.05% v/v. Each replicate plot containing one strawberry plant was caged to prevent the migration of insect populations.

Third generation laboratory reared SWD winged adults were released on each caged strawberry transplant. Adult SWD counts were recorded at before application (pre-count), 4 days after application (DAA), 7 DAA, and 11 DAA. The number of SWD larvae per berry was recorded at 14 DAA, 21 DAA, 28 DAA, and 35 DAA. Statistics were analyzed using ANOVA mean comparison with LSD test and $\alpha=0.05$.

Following the first application, MBI-203 treatments showed progressive reduction of Spotted Winged *Drosophila* adults and a rate response was observed for both DF1 and DF2 products. Although not significantly comparable to ENTRUST®, (Dow AgroBioSciences) containing spinosad as an active ingredient, MBI-203 DF2 at 4 lb/a significantly reduced adult populations by 25% in comparison to the UTC at 7 days after the first application (DAA). By 11 DAA, both DF1 and DF2 at 4 lb/a reduced adult counts by 44%, although not statistically different from the UTC. Both MBI-203 products exhibited significant results for reduction of SWD larvae counts. At all evaluations, DF2 at 4 lb/a significantly reduced the number of larvae per berry by 71%, comparable to ENTRUST®, (Dow AgroBioSciences) containing spinosad as an active ingredient, at 78%; further, by 21 DAA, larvae counts were controlled by all MBI-203 treatments up to 72%, and all were comparable to ENTRUST®, (Dow AgroBioSciences). A rate response was observed for both MBI-203 DF1 and DF2 with respect to larvae counts.

Results:

TABLE 16

Number of Flies per Tent. Average count of *Drosophila suzukii* winged adults following release onto plants and applications per treatment, listed by evaluation date.

| Trt No. | Treatment Name | Rate | Rate Unit | Appl Code | Pre-Count | 4 DAA | 7 DAA | 11 DAA |
|---|---|---|---|---|---|---|---|---|
| 1 | Untreated | | | ABC | 25.00 a | 23.25 a | 16.00 ab | 4.00 a |
| 2 | MBI-203 DF 1 | 1 | lb/a | ABC | 25.00 a | 21.25 a | 14.75 ab | 2.75 a |
|   | Silwet L77 | 0.05 | % v/v | ABC | | | | |
| 3 | MBI-203 DF 1 | 4 | lb/a | ABC | 25.00 a | 19.75 a | 13.50 ab | 2.25 a |
|   | Silwet L77 | 0.05 | % v/v | ABC | | | | |
| 4 | MBI-203 DF 2 | 1 | lb/a | ABC | 25.00 a | 21.00 a | 18.00 a | 3.00 a |
|   | Silwet L77 | 0.05 | % v/v | ABC | | | | |
| 5 | MBI-203 DF 2 | 4 | lb/a | ABC | 25.00 a | 19.75 a | 12.00 b | 2.25 a |
|   | Silwet L77 | 0.05 | % v/v | ABC | | | | |
| 6 | Entrust | 1.5 | oz/a | ABC | 25.00 a | 8.25 b | 0.00 c | 0.00 b |
|   | Silwet L77 | 0.05 | % v/v | ABC | | | | |

TABLE 17

Percent Control. Average percent control of *Drosophila suzukii* larvae per replicate plot, listed by evaluation date.

| Trt No. | Treatment Name | Rate | Rate Unit | Appl Code | 14 DAA | 21 DAA | 28 DAA | 35 DAA |
|---|---|---|---|---|---|---|---|---|
| 1 | Untreated | | | ABC | 0.00 d | 0.00 b | 0.00 b | 0.00 c |
| 2 | MBI-203 DF 1 | 1 | lb/a | ABC | 41.52 c | 54.22 a | 42.83 ab | 44.44 b |
|   | Silwet L77 | 0.05 | % v/v | ABC | | | | |
| 3 | MBI-203 DF 1 | 4 | lb/a | ABC | 54.78 bc | 67.85 a | 88.11 a | 100.00 a |
|   | Silwet L77 | 0.05 | % v/v | ABC | | | | |
| 4 | MBI-203 DF 2 | 1 | lb/a | ABC | 52.97 bc | 60.58 a | 64.33 a | 88.89 a |
|   | Silwet L77 | 0.05 | % v/v | ABC | | | | |
| 5 | MBI-203 DF 2 | 4 | lb/a | ABC | 71.36 ab | 72.16 a | 88.11 a | 100.00 a |
|   | Silwet L77 | 0.05 | % v/v | ABC | | | | |
| 6 | Entrust | 1.5 | oz/a | ABC | 78.12 a | 69.19 a | 100.00 a | 100.00 a |
|   | Silwet L77 | 0.05 | % v/v | ABC | | | | |

The findings may be summarized as follows:

A rate response was observed for MBI-203 DF1 and DF2 for reduction of SWD adults and larvae counts MBI-203 DF2 at 4 lb/a significantly reduced adult populations by 25% at 7 DAA Throughout the trial, DF2 at 4 lb/a significantly reduced the number of larvae per berry and was comparable to Entrust Although application of both products did not show much effect on adult population, it significantly reduced the larval population in the next generation.

Example 13

Repellent Effect of MBI-203 to Aphids

Evaluation of repellent effect of various concentrations MBI-203 for green peach aphids was performed. Specifically, three treatment concentrations of MBI-203 in water (1% v/v, 3% v/v and 10% v/v) were evaluated. The MBI-203 10% v/v concentration was used as positive control and dH$_2$O only treatment as negative control. Each treatment solution was added with 0.01% TWEEN 20.

Bioassays were performed by treating pepper leaf discs with respective MBI-203 concentrations as mentioned above. Pepper leaf discs (from 3-4 week old pepper plants) were cut in circles using a 23 mm cookie cutter, selecting a flat portion of the leaf to make sure the leaf disc can be evenly laid flat into the agar plate after treatment with the compound. A 1% agar solution was melted by heating and poured into the 145 mm×20 mm petri plate, enough to cover the bottom surface of the plate to prop leaf discs and maintain humidity. The agar was allowed to solidify by cooling at room temperature.

Leaf disc treatment was performed by pouring the treatment solution into a glass petri dish. With the solution in the dish, leaf discs were treated by soaking, swirling the dish gently to completely soak and coat the leaf discs. Treatment of leaf discs by soaking was done for 1 minute. Treated leaf discs were then allowed to dry off by taking them out from the solution using forceps and placing them in the fume hood for 10-15 minutes or until the solution had completely dried off in the leaf surface. Once leaf discs are dried, 40 μL water was pipeted onto the agar where leaf disc will be laid. Treated leaf discs were then laid equidistant from each other, onto the wetted surface of the agar, placing each disc abaxial side down. Each disc was pressed down gently to completely flatten into the agar, and 20 3-4 day old GPA adults were introduced at the center of the dish using a fine paint brush. Plates were then covered and sealed with parafilm. Petri plate cover was poked with tiny holes for aeration and to prevent condensation.

The test was performed in three replications. Repellency data of adults and nymphs was determined 24 hours after exposure of adults in the plates with treated leaf discs. The number of aphids (adults and nymphs) present in each leaf was counted and data recorded and analyzed.

Results

Figure 6:
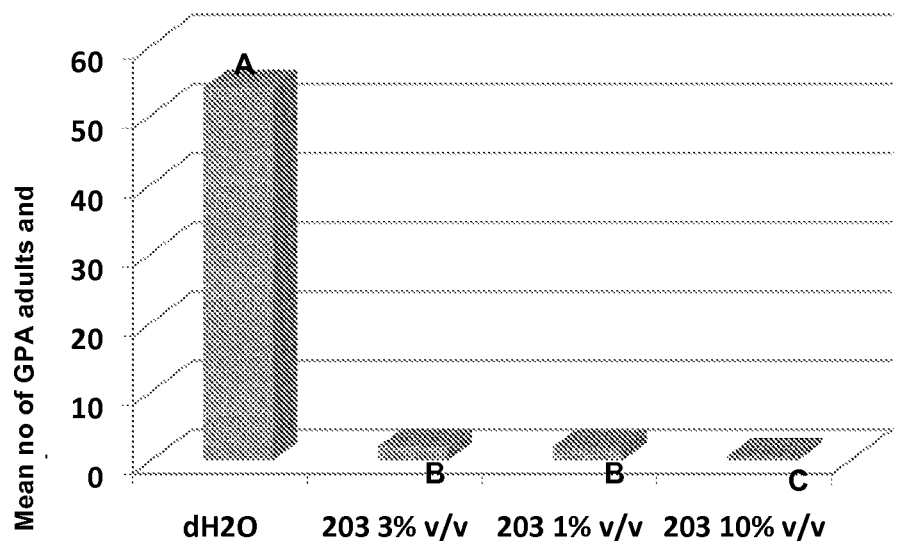

MBI-203 is repellent to GPA adults and nymphs with 97-99% repellency at different MBI-203 concentrations (Table 18). FIG. 6 shows a statistical difference among treatment concentrations. MBI-203 at 3% and 1% v/v concentrations had a computed mean % repellency of 97% and 99% repellency, respectively.

TABLE 18

Mean percent (%) repellency of Green Peach Aphid (GPA) adults and nymphs on pepper leaf discs treated with different MBI-203 concentrations.

| Treatment | % Mean Repellency |
|---|---|
| MBI-203 std 3% v/v | 97 |
| MBI-203 std 1% v/v | 99 |
| MBI-203 std 10% v/v | 97 |

Example 14

MBI-203 Application Reduces Aphid Progeny

MBI-203 at 3% v/v concentration was tested to determine the effect of the compound on the progeny production of green peach aphid (GPA) adults. Bioassays were performed by treating pepper leaf discs with MBI-203 at 3% v/v. Pepper leaf discs (from 3-4 week old pepper plants) were cut in circles using a 23 mm cookie cutter, selecting a flat portion of the leaf to make sure the disc can be evenly laid flat on the agar plate. A 1% agar solution was melted by heating and 30 μL poured in each petri plate (16 mm×35 mm vented, polystyrene petri plates), just enough to cover the bottom of the plate to prop leaf discs and maintain humidity. The agar was allowed to solidify by cooling at room temperature. Leaf disc treatment was performed by pouring the treatment solution into a glass petri dish. With the solution in the dish, leaf discs were treated by soaking, gently swirling the dish to completely soak and coat the leaf discs. Treatment of leaf discs by soaking was done for 1 minute. Treated leaf discs were allowed to dry for 10-15 minutes in fume hood or until the solution had completely dried off the leaf surface. Each treated leaf disc was laid individually onto the agar plate, placing the leaf disc abaxial side down on wetted agar, pressed down gently to completely flatten the disc into the agar. In each plate with treated leaf disc (treatment), 6 GPA adults (3-4 day old) were introduced. The plates with adult aphids were then covered with parafilm. Parafilm covers were poked with tiny holes for aeration and to prevent condensation. Plates were incubated at room temperature. Progeny (early nymphal instars) were counted 3 days after adult exposure to treated leaf discs. The experiment was done in 3 replications, and the whole experiment was repeated 5 times.

Figure 7:
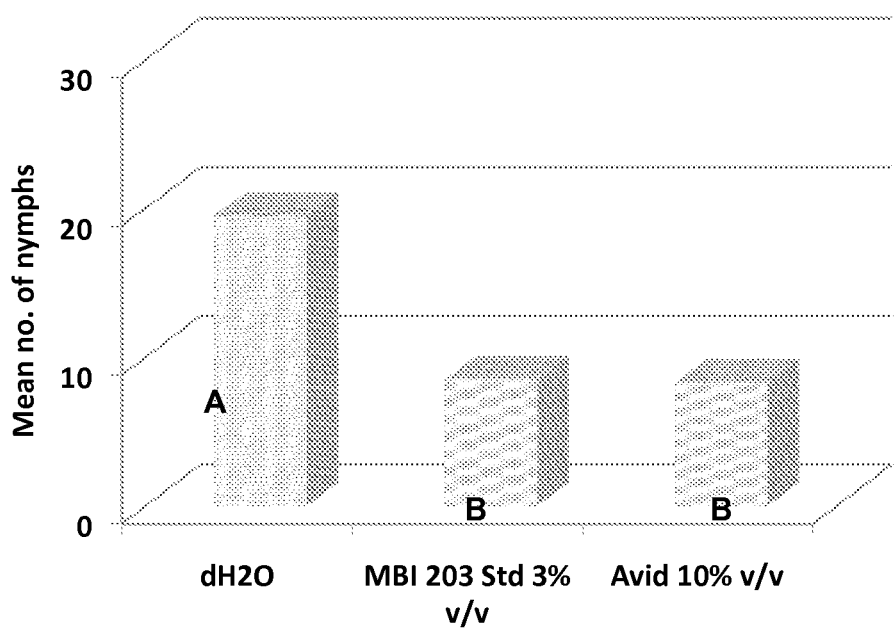
Figure 8:
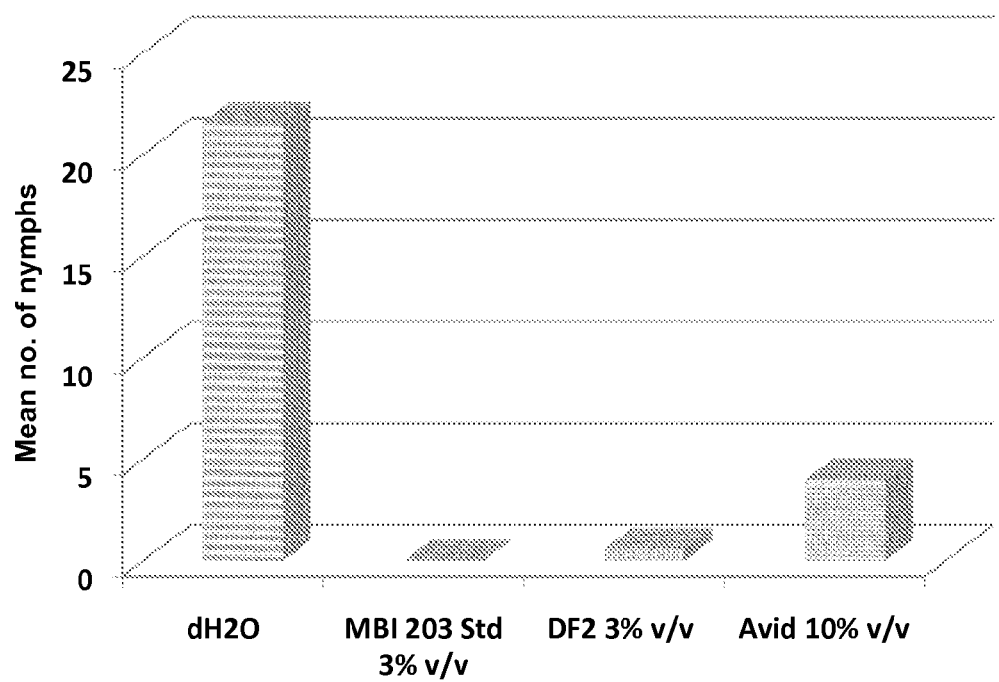
Figure 9:
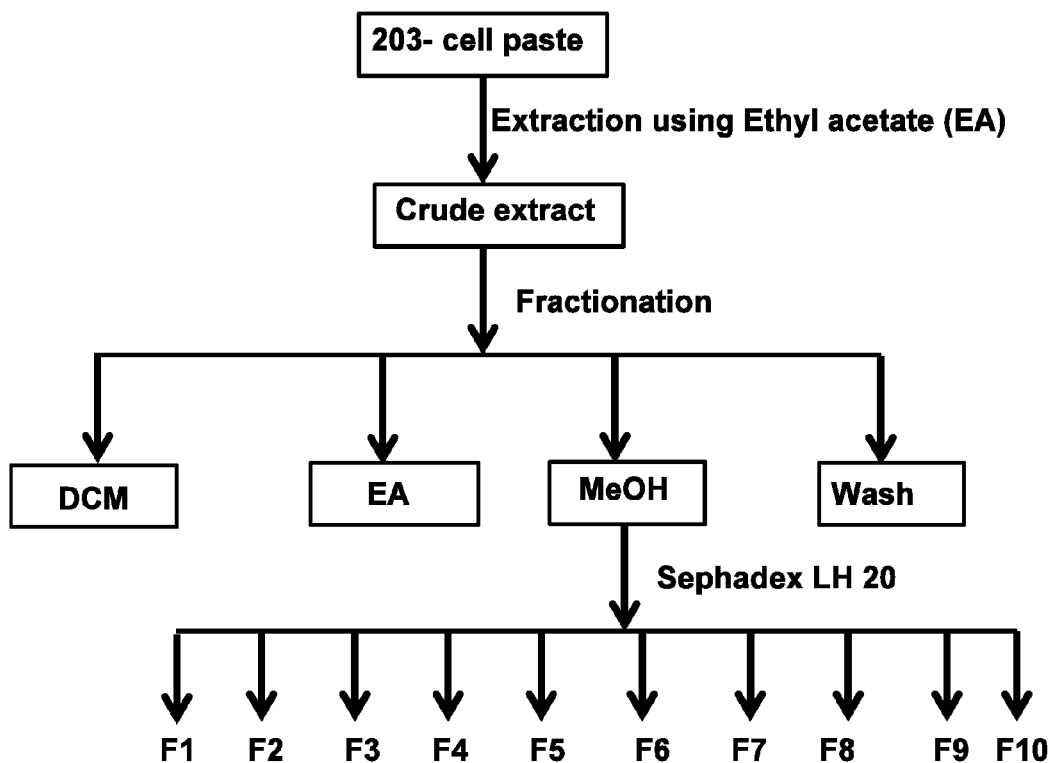
Figure 10:
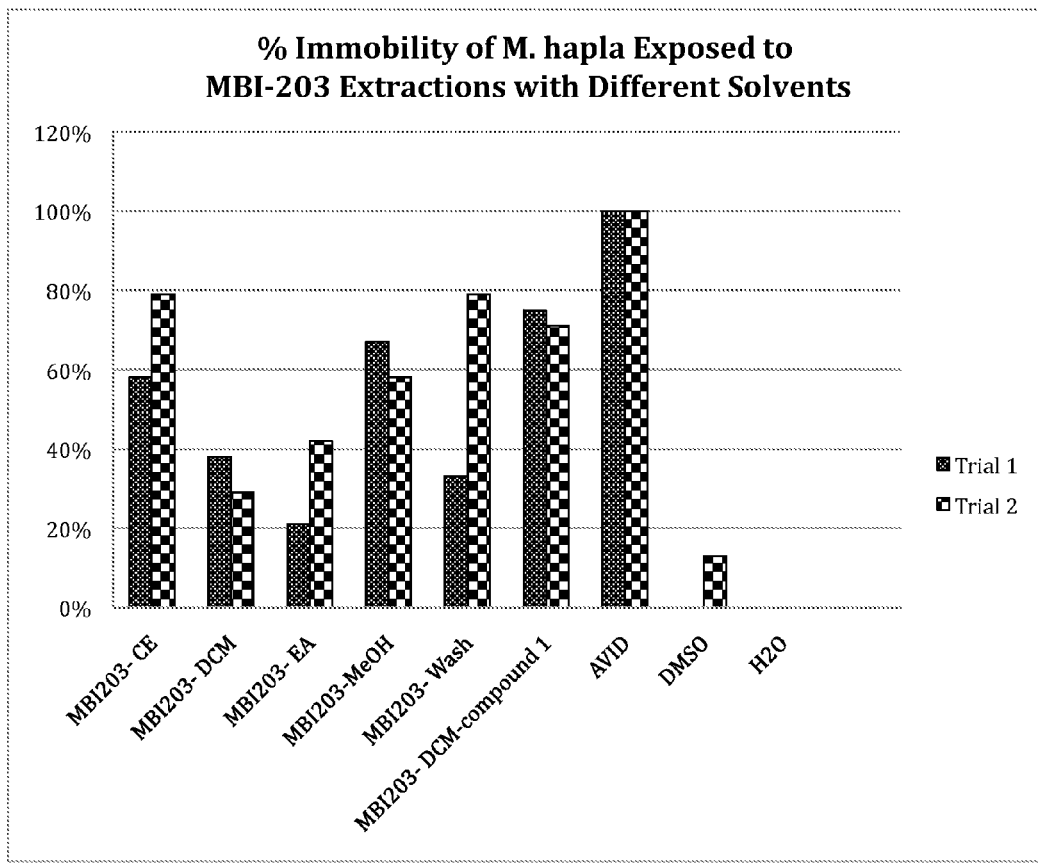

FIG. 7 shows the MBI-203 significantly affected progeny production of GPA adults 3 days post exposure to treated leaf discs. The graph in figure five is the result of the five trials conducted and reduction in progeny of GPA adults was observed to be more than 50% compared to the negative control (water only treatment) and its performance is comparable to the positive control (10% Avid), showing statistically the same in progeny production. When the number of progeny production was tested in comparison with the formulated product DF2, there was no statistical difference between MBI-203 standard and DF2 at 3% v/v concentration (FIG. 8). A progeny (nymphs) reduction of more than 90% was exhibited in MBI-203 and DF2 treatments compared from the negative control, which showed to be significantly better than Avid at 10% v/v concentration (positive control).

Example 15

Extraction of Violacein and Oligo-((1-Hydroxybutyric Acid) from *Chromobacterium substugae*

The following procedure was used for the purification of compounds extracted from the culture of *Chromobacterium substugae:*

The whole culture broth (WCB) derived from the 20-L fermentation C. substugae in L-broth was extracted by liquid-liquid extraction method using ethyl acetate. The ethyl acetate layer was separated and dried under vacuum using rotary evaporator to give the crude extract. The crude extract was then fractionated by using different solvent such as dichloromethane (DCM), ethyl acetate (EA), methanol (MeOH) and washing with mixture of solvent (WASH). These fractions were then concentrated to dryness using rotary evaporator and the resulting dry residues are screened for biological activity using different pest (insects, nematodes). The active fractions were then subjected to Sephadex LH 20 size exclusion chromatography ($CH_2Cl_2/CH_3OH$; 50/50) to give 10 fractions (FIG. 9). These fractions were then concentrated to dryness using rotary evaporator and the resulting dry residues (fractions) were screened for biological activity using insect repellency assay with green peach aphids, progeny production of green peach aphid (GPA) and nematicidal bioassay (*M. incognita* and/or *M. hapla*). The active fractions were then subjected to reversed phase HPLC (Spectra System P4000 (Thermo Scientific) to give pure compounds, which were then screened in above mentioned bioassays to locate/identify the active compounds. To confirm the identity of the compound, additional spectroscopic data such as LC/MS and NMR were recorded.

The potent insecticidal repellent compound was isolated from fractions F8, F9 & F10 and was identified as violacein (2). The nematicidal active compound from the main DCM fraction was identified as oligo-(β-hydroxybutyric acid) (4).

Mass Spectroscopy Analysis of Compounds

Mass spectroscopy analysis of active peak was performed on a Thermo Finnigan LCQ Deca XP Plus electrospray (ESI) instrument using both positive and negative ionization modes in a full scan mode (m/z 100-1500 Da) on a LCQ DECA $XP^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5μ 100 A column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 μL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The analysis of oligo-(β-hydroxybutyric acid) (1) was performed using LTQ Orbitrap XL hybrid Fourier Transform Mass Spectrometer at UC Davis Mass spectrometry facility.

NMR Spectroscopy Analysis of Compounds

NMR-NMR spectra were measured on a Bruker 600 MHz gradient field spectrometer. The reference is set on the internal standard tetramethylsilane (TMS, 0.00 ppm).

Purification of Compounds

The dichloromethane (DCM) fraction was triturated with methanol and the white solid obtained was filtered off to give oligo-(β-hydroxybutyric acid) (1).

Identification of Compounds

Oligo-(β-hydroxybutyric acid) (1)

The $^1H$ NMR spectrum of compound 4 exhibited signals at δ 5.22 (sext), 2.62 (dd) and 2.53 (dd) with a relative intensities of 1 proton each. In addition to these a methyl signal at δ 1.31 as a doublet was also observed. The $^{13}C$ NMR spectrum showed only four carbon signals at δ 169.2, 67.6, 40.9 and 19.8. The detail 1D & 2D NMR analysis resulted to the partial structure of $-(-O-CHCH_3-CH_2-CO-)-$ with a fragment mass of 86. The MALDI-TOF-ESI MS (FIG. 2) of this compound exhibited typical signal pattern as for a mixture of oligomers with molecular masses of [(n×86)+Na], corresponding the product was a mixture of Oligo-(β-hydroxybutyric acid) 1 with n=10-25. This compound has been reported to be isolated from several bacteria (Singh et al., 2011; Maskey et al., 2002; Hahn et al., 1995). Potency of this compound obtained from DCM fraction was confirmed in an in vitro assay using *M. hapla* which showed 75% immobility (FIG. 10).

In Vitro Testing of Fractions and Pure Compound of *Chromobacterium substugae.*

The fractions and pure compounds were dissolved in Dimethylsulfoxide (DMSO) and were tested in an in vitro 96-well plastic cell-culture plate bioassay. Around 15-20 nematodes in a 50 μl water solution were exposed to 100 μl of a 4 mg/ml of sample for a 24 hour period at 25° C. Once the incubation period was completed, results were recorded based on a visual grading of immobility of the juvenile nematodes (J2's) in each well treated with samples; each treatment was tested in well repetitions of four. Results were shown in FIG. 5, which shows the results of two different 96-well plate bioassays of *C. substugae* fractions and compound 4. Three controls were included in each trial; 1 positive (1% Avid) & 2 negative (DMSO & water). Both trials (T1) and (T2) were carried out using *M. hapla* nematodes.

Isolation and Identification of Compounds Responsible for Repellency

The main fractions such as DCM, EA, MeOH and WASH were tested for repellency activity using the green peach aphid (GPA) bioassay as described in detail below. The most potent repellency was observed for EA and MEOH fractions. The LCMS analysis of these fractions showed similar chemical profile, so since the yield of MeOH fraction was higher than EA fraction, the detail chemistry work was carried out using MeOH fraction. The MeOH fraction further fractionated using Sephadex LH 20 size exclusion chromatography ($CH_2Cl_2/CH_3OH$; 50/50) to give 10 fractions (FIG. 9). The most potent activity was observed in factions F9 and F10. Bioassay guided purification of these fractions by combination of HPLC and Sephadex LH 20 gave violacein as the compound responsible for repellent activity. Violacein was also tested in aphid progeny testing.

Example 16

Repellent Effect of MBI-203 Fractions on Green Peach Aphid

Methods

Choice bioassays on Green Peach Aphid adults (GPA) were done using MBI-203 fractions and pure compound. Fractions and pure compound (violacein) obtained from the extraction of cell paste of *C. substugae* (MBI-203) were tested for insect efficacy through repellency bioassays. Pepper leaf discs (from 3-4 week old pepper plants) were cut in circles using a 23 mm cookie cutter, selecting a flat portion of the leaf to make sure the leaf disc can be evenly laid flat into the agar plate after treatment of the compound. One percent (%) agar in water was prepared. The 1% agar solution was melted by heating and poured into the 145 mm×20 mm petri plate, enough to cover the bottom surface of the plate to prop leaf discs and maintain humidity. The agar was allowed to solidify by cooling at room temperature.

Leaf disc treatment was done by pipetting gently 100 µL of MBI-203 extract unto the underside of the leaf disc. Treated leaf discs were then allowed to dry off by laying the disc flat unto a labeled 12-well plate cover. Once leaf discs are dried, 40 uL water was pipetted unto the agar where leaf disc will be laid. Treated leaf discs were then laid equidistant from each other, unto the wetted surface of the agar, placing each disc abaxial side down with the treated surface up. Each disc was pressed down gently to completely flatten into the agar. After laying treated leaf discs, 20 3-4 day old GPA adults were introduced at the center of the dish using a fine paint brush. Plates was then covered and sealed with parafilm. Petri plate covers were poked with tiny holes for aeration and prevent condensation.

All tests were done in three replications. To select the solvent for testing initial testing of the crude extract was done using methanol and acetone as a solvent. This test showed that acetone was better as a solvent. Succeeding samples testing including fractions and pure compound (violacein) were carried out using acetone as a solvent. Data for repellency of adults and nymphs was determined 24 hours post exposure of adults on treated leaf discs. The number of aphids (adults and nymphs) was counted and data recorded and analyzed. The percent repellency was computed as:

$$\% \text{ Repellency} = 100 - \{([N+A]\text{"on treated leaf"})/[N+A]\text{"on petri dish"} \times 100\},$$

where A stands for adults and N stands for nymphs.

Results

Figure 11A:
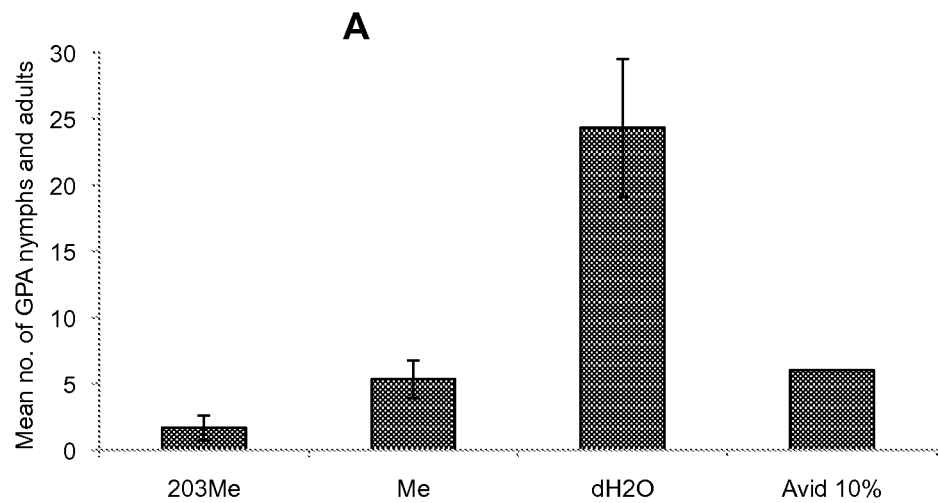
Figure 11B:
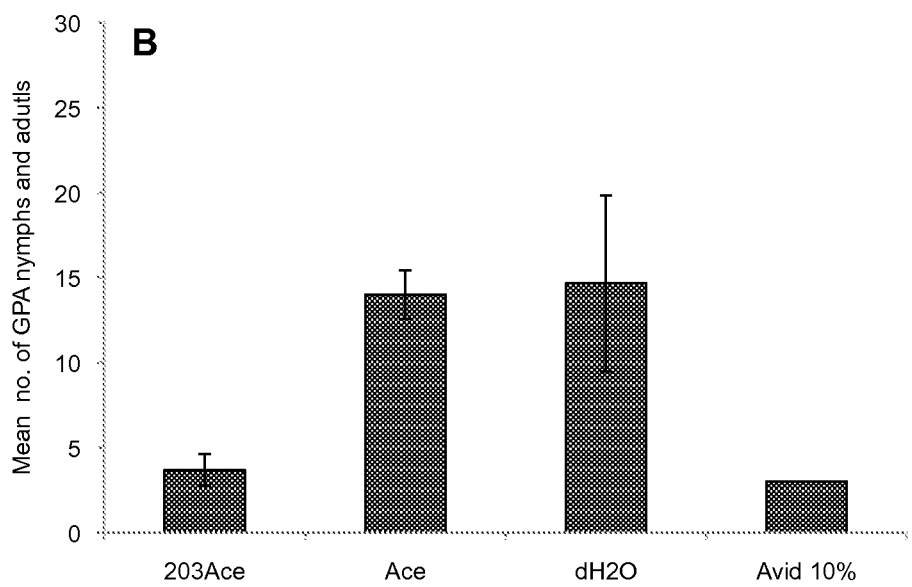

Repellency tests for MBI-203 fractions started with the crude extracts. Crude extracts in methanol and acetone solvents were tested and analysis of result showed significant differences as shown in FIG. 11. Leaf discs treated with crude extract of MBI-203 in both methanol and acetone solvents resulted in a statistically significant difference in settling response of green peach aphid nymphs and adults than those of the negative control. FIGS. 11A and B showed a repellent effect of MBI-203 on the aphids. The methanol solvent however showed a repellent effect on aphids (FIG. 11A), showing no statistical difference with the MBI-203 extract and the positive control (avid 10%). The solvent acetone showed to be a good solvent to use in fractions as it did not exhibit repellency on GPA nymphs and adults, having the mean number of nymphs and adults settling in the leaf disc statistically the same with the negative control (FIG. 11B).

Figure 12A:
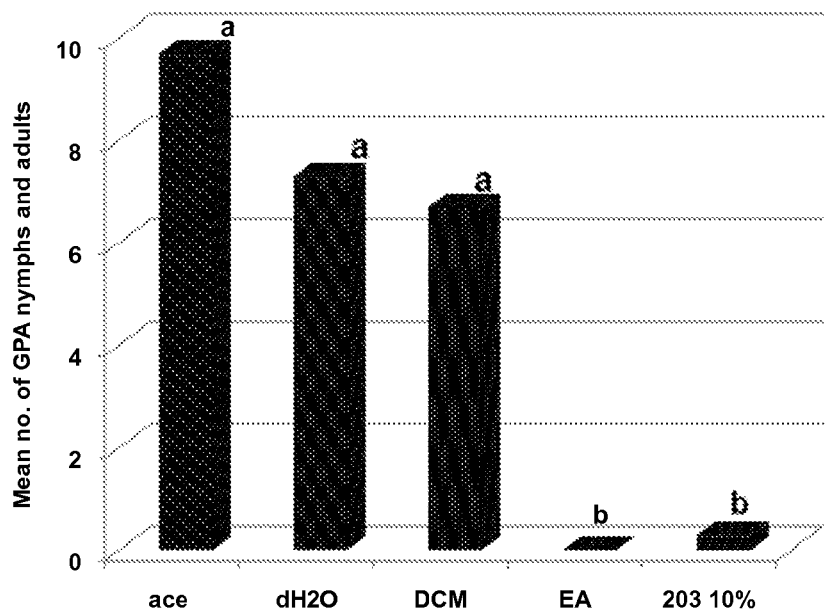
Figure 12B:
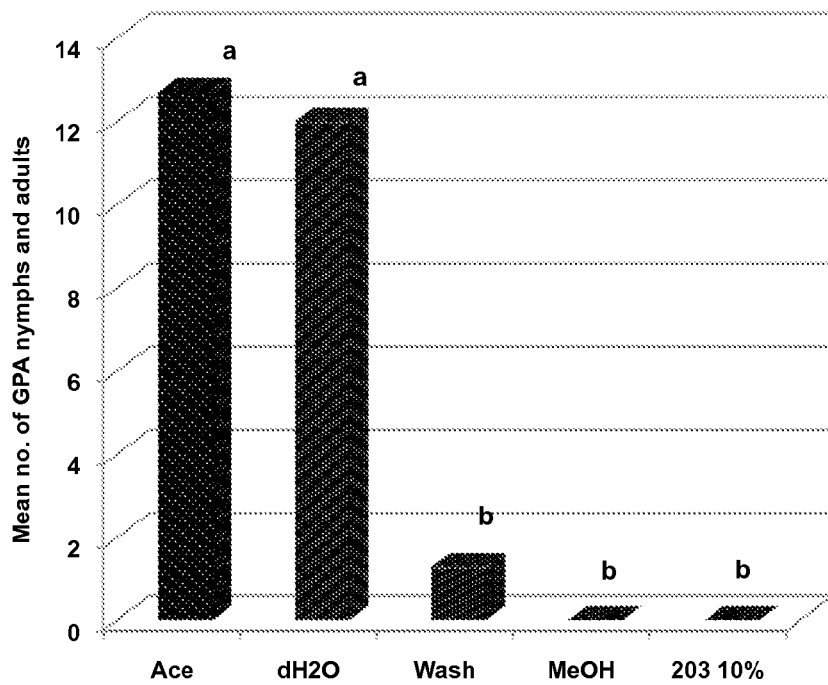

Fractions of MBI-203 exhibited a strong repellency on GPA nymphs and adults. Statistical difference among treatment means were observed (FIGS. 12A and B). Fractionated materials EA and MeOH caused 100% repellency on nymphs and adults while Wash material 94% repellency which is not statistically different from the positive control (MBI-203 10% v/v) (Table 19).

TABLE 19

Mean percent repellency of MBI-203 fractionated samples.

| Fractionated material | Mean % Repellency |
| --- | --- |
| DCM | 77.2 |
| EA | 100 |
| 203 10% (+C) | 98.9 |
| Wash | 94 |

TABLE 19-continued

Mean percent repellency of MBI-203 fractionated samples.

| Fractionated material | Mean % Repellency |
| --- | --- |
| MeOH | 100 |
| 203 10% (+C) | 100 |

Furthermore, the 10 fractions obtained from MeOH fraction were tested using acetone as a solvent; the samples with pure violacein compound (F9, F10) showed high repellency effect on adults and nymphs of green peach aphids (Table 20). Only 2 non-violacein fractions showed high repellency effect (F2 and F3). The fractions F9 and F10 were further purified which gave violacein which had 100% repellency. The data revealed that violacein is the responsible compound in causing repellency to sucking insects. It appears that fractionated materials F6-F10 contained violacein with F9 and F10 containing pure violacein compound.

TABLE 20

Mean percent repellency of fractions obtained from fractionation of MeOH fraction (F1-F10).

| Fractionated material | Mean % Repellency |
| --- | --- |
| F1 | 81.5 |
| F2 | 92.9 |
| F3 | 95.6 |
| F4 | 76.8 |
| F5 | 84.3 |
| F6 | 90.1 |
| F7 | 96 |
| F8 | 91.5 |
| F9 | 100 |
| F10 | 100 |

Example 17

Violacein Reduces Aphid Progeny

Two concentrations of pure violacein compound in acetone, 0.5 µg/mL and 1.0 µg/mL were used in the test to determine the effect of the compound on the progeny production of green peach aphid (GPA) adults. Bioassays were performed by treating pepper leaf discs with the different violacein concentrations in acetone. Pepper leaf discs (from 3-4 week old pepper plants) were cut into 23 mm diameter discs, selecting a flat portion of the leaf to make sure the disc can be evenly laid flat onto the agar plate after treatment with the compound. A 1% agar solution was prepared, melted by heating and 30 µL poured into petri dishes (16 mm×35 mm vented, polystyrene petriplates), just enough to cover the bottom of the plate to support leaf discs and maintain humidity. The agar was allowed to solidify by cooling at room temperature. Treatment with violacein was done by gently spreading 100 µL of the sample solution onto the leaf disc using a 200 µL pipetman. Treatments were set up in triplicate. Treated leaf discs were allowed to dry in the hood for 5-10 minutes. The positive control was 10% v/v Avid and the negative control was $dH_2O$, acetone was used as the blank. In each solidified agar plate, 20-30 µL $dH_2O$ was pipetted onto the agar to maintain humidity. Each treated leaf disc was laid individually onto the agar plate, placing the leaf disc abaxial side down on wetted agar, pressed down gently to completely flatten the disc onto the agar. In each plate with treated leaf disc (treatment), 6 GPA adults (3-4 day old) were introduced. The plates with adult aphids were then covered with parafilm.

Cover parafilm was poked with holes aeration to prevent condensation, and was kept at room temperature. Progeny (early nymphal instars) were counted 3 days after adult exposure to treated leaf discs. The experiment was done in 3 replications, and the whole experiment was repeated 2 times.

Figure 13:
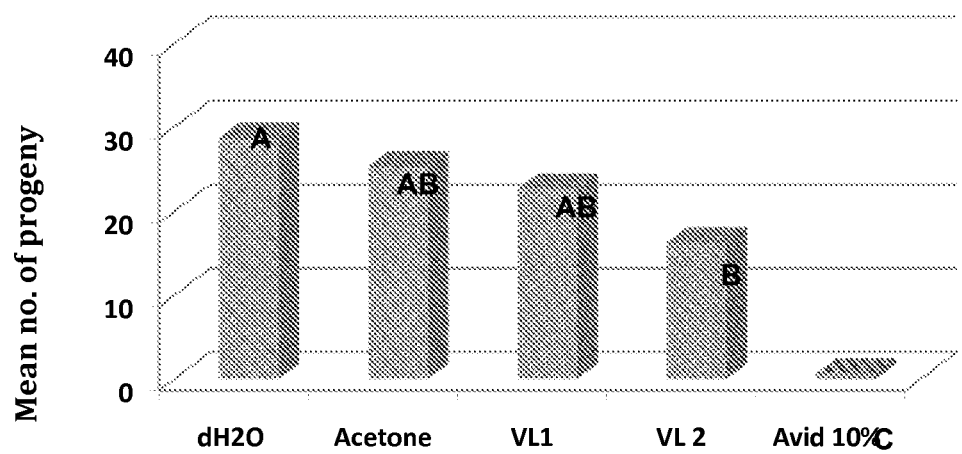

As shown in FIG. 13, violacein at 1.0 µg/mL significantly reduced progeny production of adult aphids. A reduction of about 50% was observed compared to the negative control (water only treatment). The positive control (10% Avid) had the least number of progeny as most of the exposed adults died 3 days post exposure. Two trials were performed in this experiment, each treatment replicated three times. Both trials provided consistent results with violacein significantly affecting progeny.

Example 18

Other Violacein Producers Display Repellency Against Aphids

The repellent effect of other *Chromobacterium* species on green peach aphids was also evaluated. *Chromobacterium* species evaluated are: *Chromobacterium piscinae* DSM 23278, *C. pseudoviolaceum* DSM 23279, *C. haemolyticum* DSM 19808 and *C. aquaticum* DSM 19852. Two of the species are violacein producing species (*C. piscinae* and *C. pseudoviol*) while the two other species are documented to not produce violacein. Microorganisms were grown on LB broth at 26° C., and 100 rpm for 5 days. At the end of the fermentation, broths were harvested and aliquoted for bioassay. Treatment concentrations at 5% v/v in water were tested on GPA adults. MBI-203 10% v/v concentration was used as positive control and dH2O only treatment as negative control. Each treatment solution was added with 0.01% TWEEN 20.

Bioassays were performed by treating pepper leaf discs as previously described. Each treated disc was pressed down gently to completely flatten into the agar. After laying treated leaf discs, 20 3-4 day old GPA adults were introduced at the center of the dish using a fine paint brush. Plates were then covered and sealed with parafilm. Petri plate covers were poked with tiny holes for aeration and to prevent condensation.

The test was done in three replications. Repellency data of adults and nymphs was determined 24 hours after exposure of adults into the plates with treated leaf discs. The number of aphids (adults and nymphs) settled on each leaf disc was counted and data recorded and analyzed. Percent repellency was calculated as follows:

$$\% \text{ Repellency} = 100 - \left\{ \frac{[N+A] \text{ on treated leaf}}{[N+A] \text{ on petri dish}} \times 100 \right\}$$

Where N=number of nymphs, and A=number of adult aphis

Figure 14:
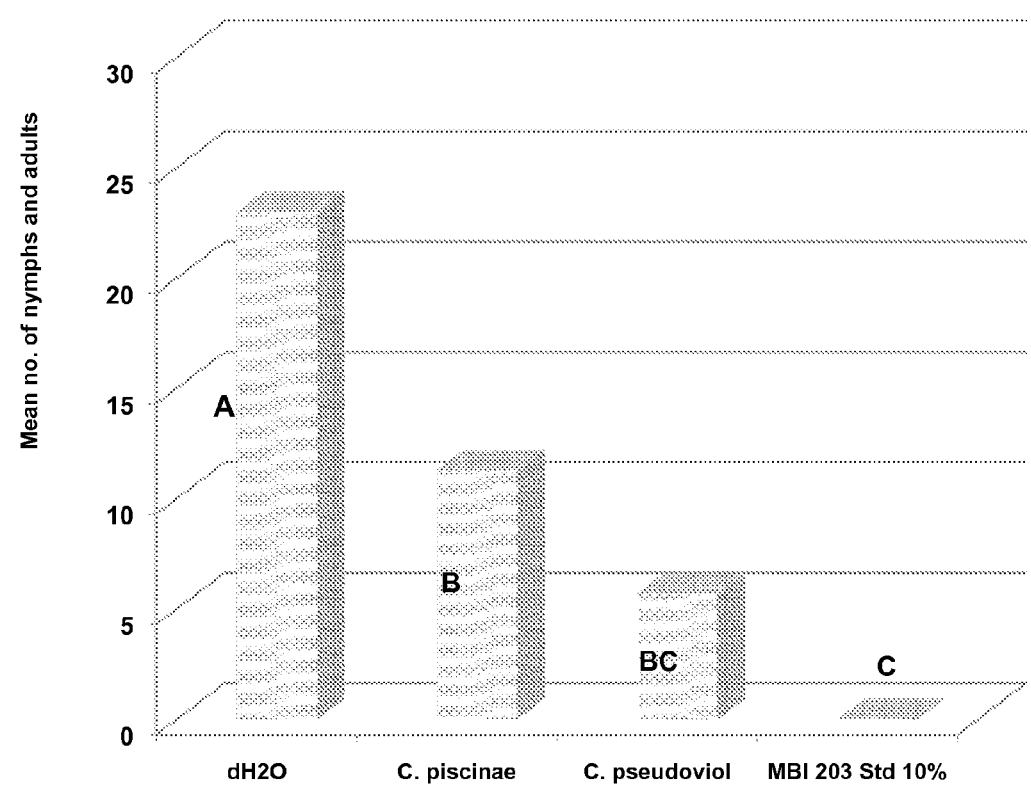
Figure 15:
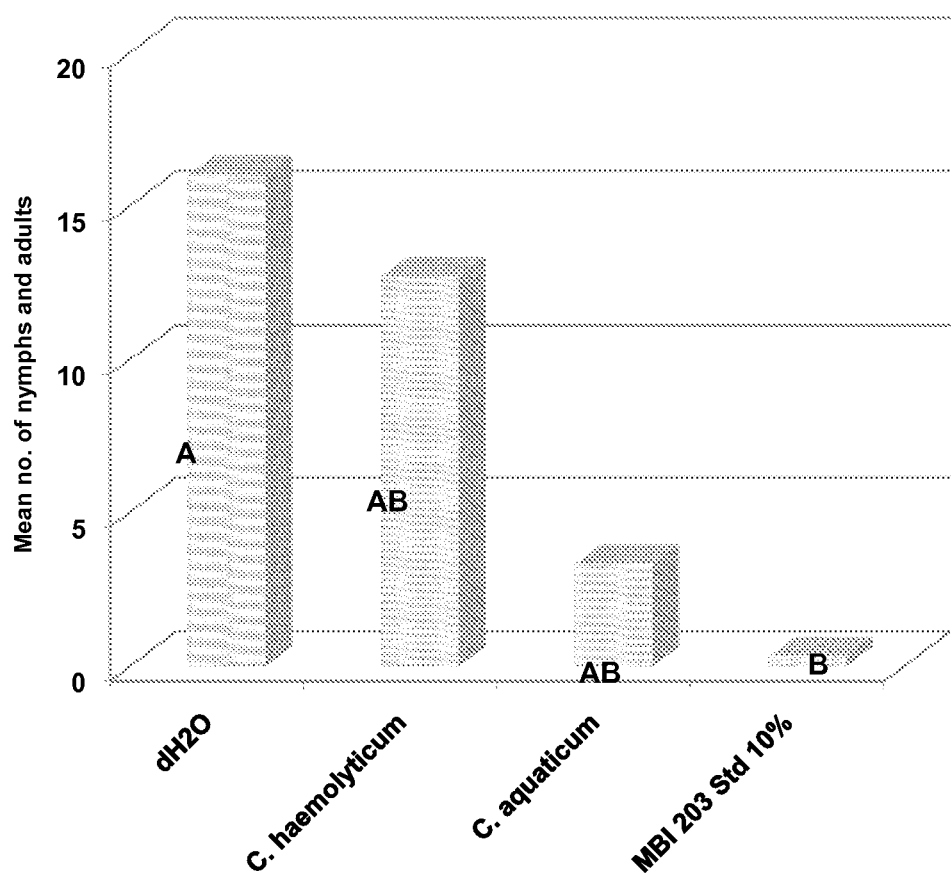
Figure 16:
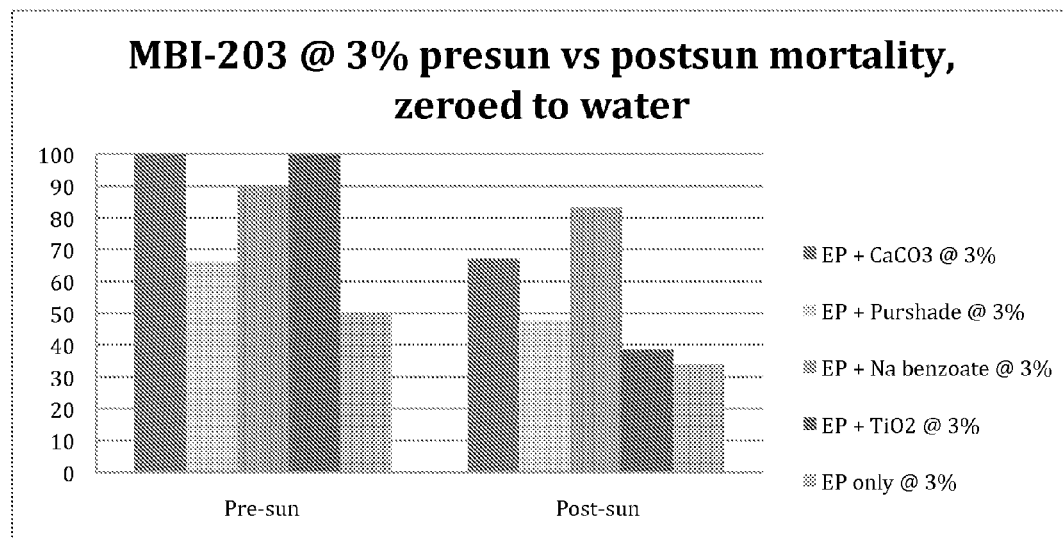
Figure 17:
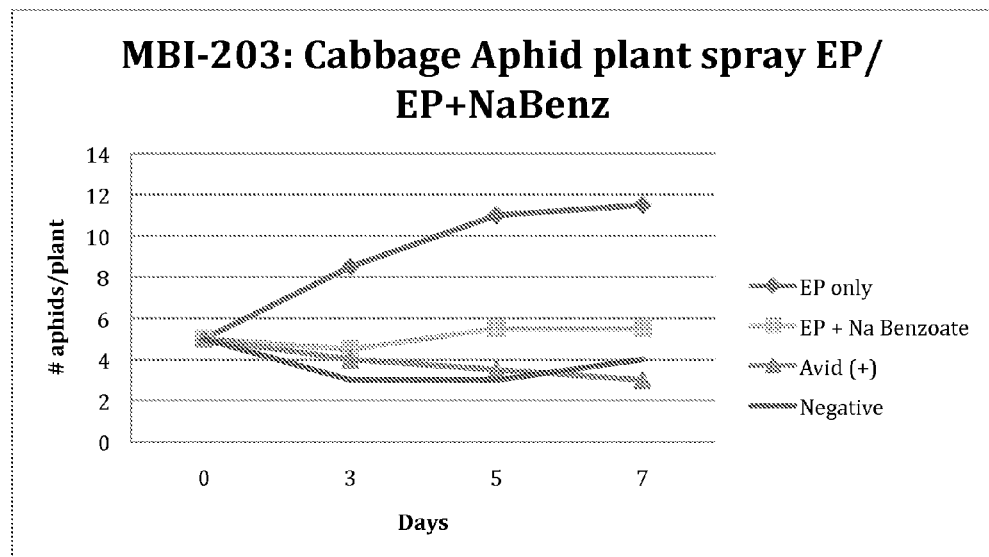
Figure 18:
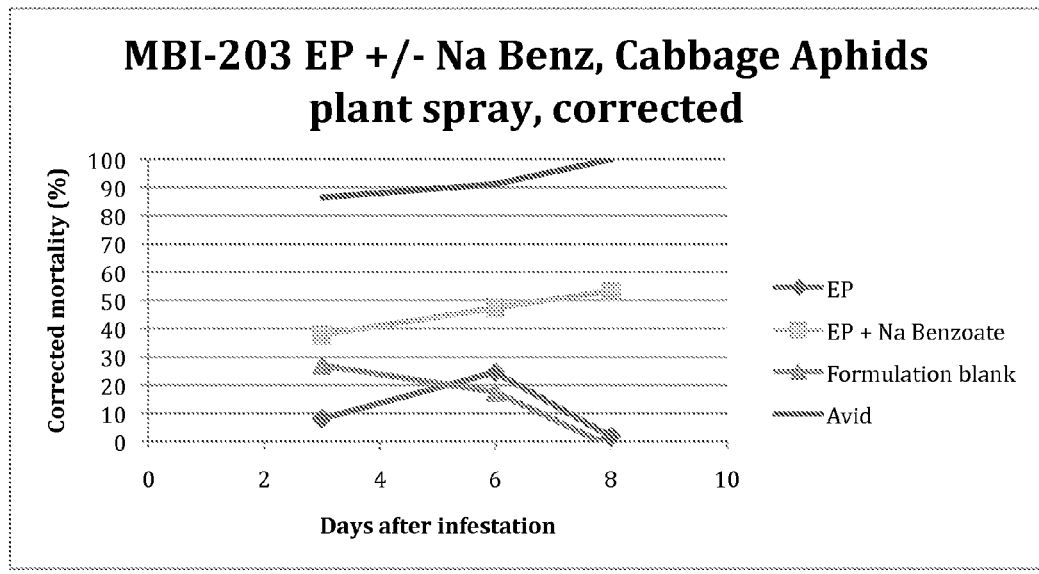
Figure 19:
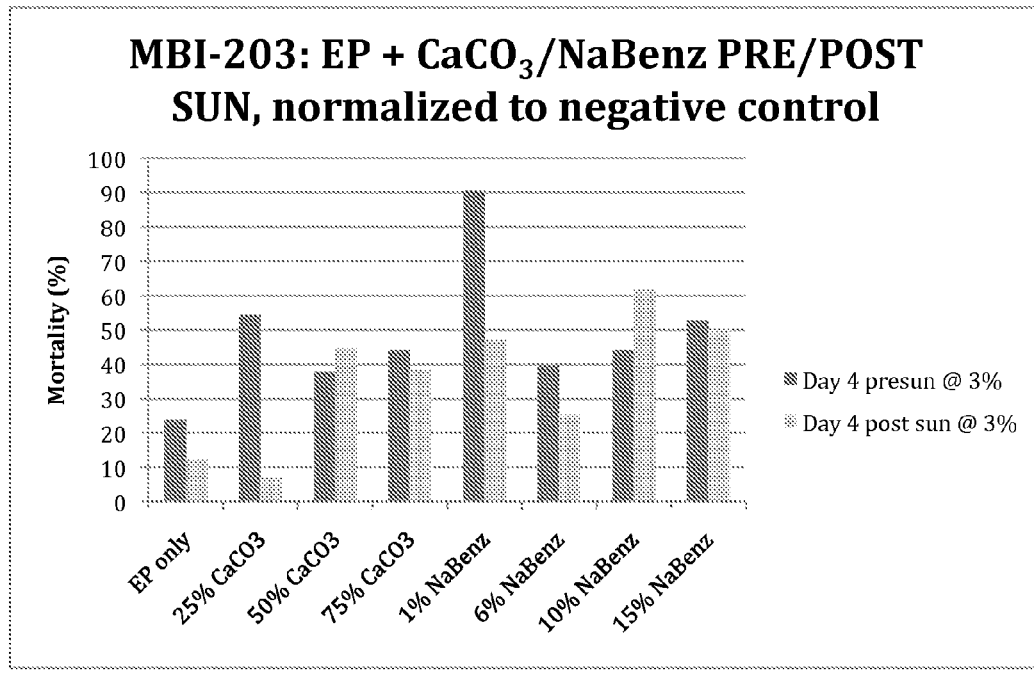
Figure 20:
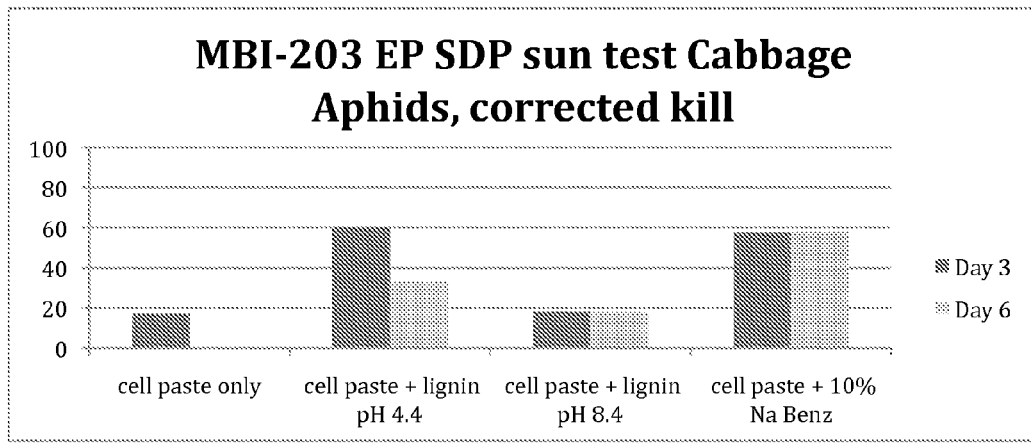
Figure 21:
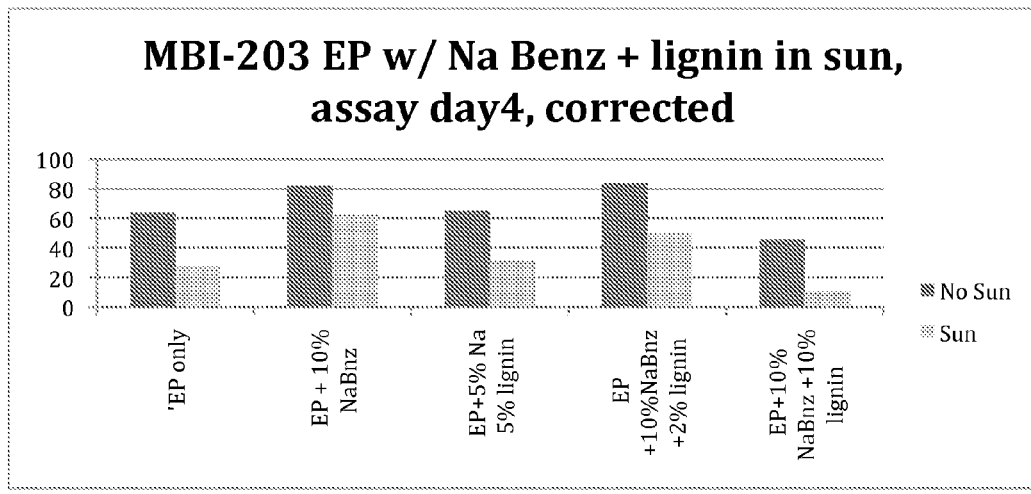
Figure 22:
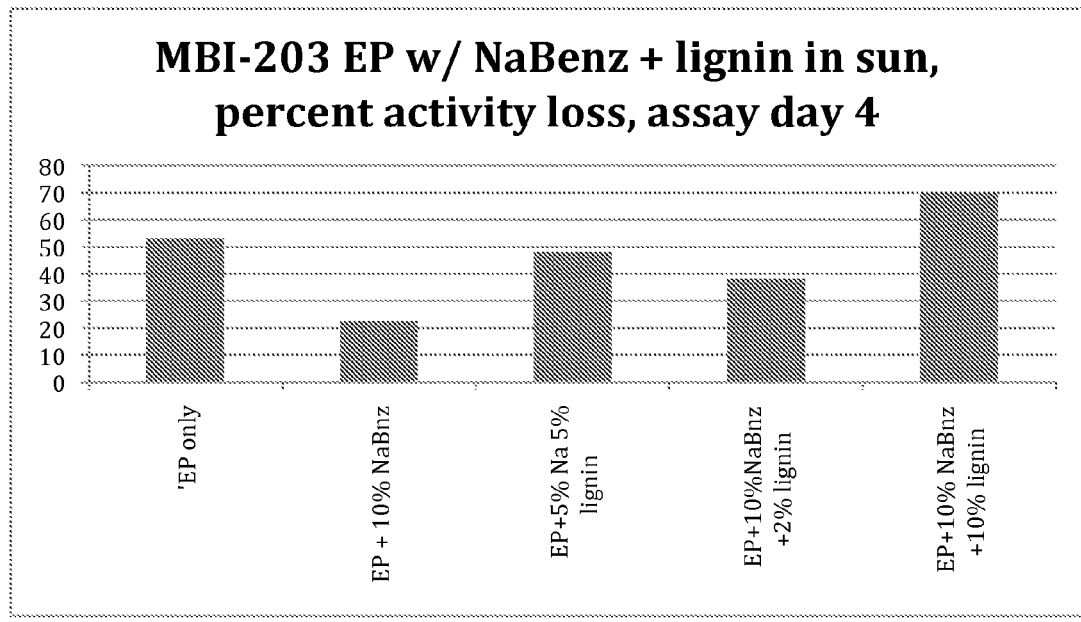
Figure 23:
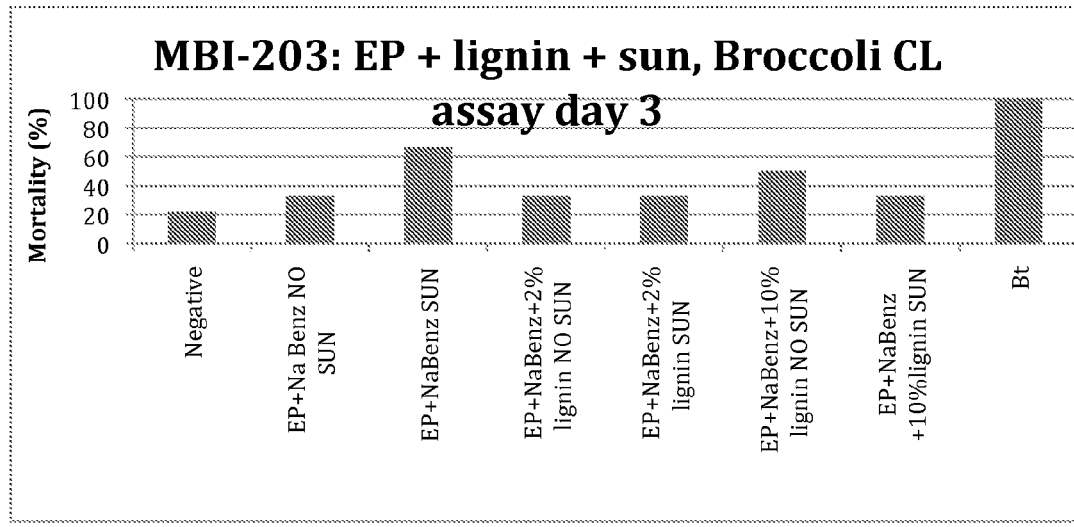

Results are shown in Tables 21 and 22 and FIGS. 14 and 15. Several violacein-producing *Chromobacterium* species showed repellency to GPA adults and nymphs with statistical differences among treatment means. *Chromobacterium* species producing violacein had mean % repellency of 75% (*C. piscinae*), 86% (*C. pseudoviolaceum*), while non-violacein producers (*C. aquaticum* and *C. haemolyticum*) were not statistically different from the untreated control (water). A slight trend of repellency was observed for the non-violacein producers.

TABLE 21

Mean percent (%) repellency of Green Peach aphid (GPA) adults and nymphs exposed to pepper leaf discs treated with different *Chromobacterium* species.

| Treatment | Mean % Repellency |
|---|---|
| *C. piscinae* | 75 |
| *C. pseudoviolaceum* | 86 |
| MBI-203 Std 10% | 100 |

TABLE 22

Mean percent (%) repellency of Green Peach aphid (GPA) adults and nymphs exposed to pepper leaf discs treated with different *Chromobacterium* species

| Treatment | Mean % Repellency |
|---|---|
| *C. aquaticum* | 91.4 |
| *C. haemolyticum* | 67.3 |
| MBI-203 Std 10% | 99 |

Example 19

Comparison of Stability of *Chromobacterium* Formulation with and without Sodium Benzoate Formulation 1 contains *Chrombacterium* cell concentrated harvest 32 parts, *Chrombacterium* Fermentation Broth Supernatant 62.5 parts, n-Hexanol 1 part, Sodium Alginate 0.5 parts, Sorbitan Ester Ethoxylate 2 parts, and d-limonene 2 parts. These formulation ingredients are chosen for their functionality in ensuring uniform and stable mixtures and are also preferred due to their listing on US EPA list 4. A listing of an ingredient on EPA list 4 deems that it is of minimal concern in terms of effect on the environment and toxicology. Formulation 2 contains *Chrombacterium* Cell concentrated harvest 32 parts, *Chrombacterium* Fermentation Broth Supernatant 54.5 parts, n-Hexanol 1 part, Sodium Alginate 0.5 parts, Sorbitan Ester Ethoxylate 2 parts, and Sodium Benzoate 10 parts.

Table 23 illustrates results of storage of formulations 1 & 2 over and extended period of time.

TABLE 23

Storage of Formulations 1 and 2

| Formulation | Visual Observation: One day | 30 days | 120 days |
|---|---|---|---|
| Formulation 1 | Uniform purple liquid | Separation of white light brown layers on top. Reduced purple color | Non uniform Grey brown liquid with white crusting in head space. |
| Formulation 2 | Uniform purple liquid | Uniform purple liquid | Uniform purple liquid |

Formulation 2 is more stable than Formulation 1. It appears that water soluble salts of benzoic acid stabilizes biological pesticide compositions against physical separation and loss of activity due to exposure to sunlight. The benzoate ions provide solvency and electrolyte balancing properties such that the biological matrix remains uniform this results in extended shelf life for the pesticide composition. The benzoate ions also provide ultraviolet radiation absorption for the product once it has been applied to field crops. The UV protection extends the insecticide activity for at least several more days.

Example 20

Effect of Sodium Benzoate on Pest Mortality

The end product MBI-203 containing *Chromobacterium substugae*, d-limonene, hexanol, propylene glycol, and paraben formulation (MBI-203 EP) combined with calcium carbonate, sodium benzoate, or titanium oxide were placed into plastic petri dishes and sealed with parafilm. Plates were placed outside for 7 hours in the sunlight. After exposure to sun, material was brought inside and diluted to 1.5% and 3% v/v concentrations with autoclaved Millipore water. Material was then placed on artificial diet, dried, and fed to neonate Cabbage Looper, *Trichoplusia ni*. Mortality was scored 3 and 4 days after infestation of diet. The results are shown in Table 24 and FIG. 16.

TABLE 24

Effect of Sodium Benzoate on Pest Mortality

| Composition | Mortality (% loss) |
|---|---|
| EP + $CaCO_3$ | ~30% loss |
| EP + $TiO_2$ | ~60% loss |
| EP + Purshade | ~25% loss |
| EP + Na benzoate | ~10% loss |
| EP only | ~30% loss |

Broccoli Study 4-5 week old Packman broccoli were sprayed with 3% v/v dilutions of MBI-203 end product (d-limonene formulation) (MBI-203 EP) with and without sodium benzoate. Each plant in a 9 $in^2$ pot received 500 uL of treatment. Tween-20 at a final concentration of 0.01% was included in all samples. Five adult Cabbage Aphids, *Brevicoryne brassicae*, were placed on each plant. Plants and insects were incubated under growth lights (75-85° F., 16 h light/8 h dark). Alive Aphids were scored 3, 5, and 7 days after infestation. It appeared that the sodium benzoate formulation provided better control than the end product alone (FIG. 17).

Red Cabbage Study

10% v/v dilutions of MBI-203 end product (d-limonene formulation) (MBI-203 EP) with and without sodium benzoate were sprayed onto Red Cabbage at approximately 30 gal/acre treatment rates. A formulation blank (lot 2403-83-3) at 10% v/v was also included in the assay. After plants had dried, they were infested with 10 Cabbage Aphids. The assay was scored on days 3, 6, and 8. Percent control was determined by applying the Henderson-Tilton correction. The results are shown in FIG. 18. The end product+sodium benzoate formulation had better control of aphids than the end product alone or the formulation blank alone.

Example 21

Comparison of Sodium Benzoate and Calcium Carbonate

Undiluted MBI-203 end product (MBI-203 EP) with various concentrations of sodium benzoate or calcium carbonate were exposed to sunlight for 1 day in sealed plastic petri dishes. Sun-exposed and unexposed material were then diluted to 3% v/v dilutions and applied to artificial diet. Neonate Cabbage Loopers were exposed to diet and mortality was scored 4 days after infestation of diet. Results are shown in FIG. 19. Sodium benzoate at 10% and 15% concentrations appeared to provide the least degradation in activity at the most economical price.

Example 22

Effect of Lignin Sulfonate

Undiluted spray dried cells with various additives were poured into a plastic vial and exposed to the environment for 4 days, 40-65° F., sunny with some days of sprinkles). Exposed and unexposed samples were diluted to 6% v/v and sprayed onto Packman Broccoli plants. Dried plants were infested with 5 immature Cabbage Aphids. Aphids were scored 3 and 6 days after infestation. Control was determined by applying the Henderson-Tilton correction. Spray dried cells with sodium benzoate had one of the highest kills at day 3 and maintained control as the assay continued to day 6 (see FIG. 20).

MBI-203 end product (d-limonene formulation) (MBI-203 EP) was mixed with various concentrations of sodium benzoate and lignin sulfonate. Treatments were diluted to 10% v/v concentrations and pipetted into plastic petri dishes and exposed to sunlight for 4 continuous days. Samples were then tested for Cabbage Looper activity by treating artificial diet. Lignin sulfonate treatments tended to form a crust over on top of artificial diet. End product with only sodium benzoate seemed to have the most promising kill before and after sun exposure (see FIGS. 21 and 22).

In another study, 10% v/v dilutions of MBI-203 end product (d-limonene formulation) with 10% sodium benzoate and various concentrations of lignin sulfonate were exposed to sunlight for 4 consecutive days in sealed plastic petri dishes. After exposure, 4 week old Packman Broccoli were sprayed with treatments at approximately a 30 gal/acre rate. Three late second instar Cabbage Looper larvae were placed on each treated plant and mortality was scored on days 3 and 4 of the assay. Of the plants in the sun, the sodium benzoate only sample had the highest control (see FIG. 23).

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

REFERENCES CITED

Asolkar, R. N., Jensen, P. R., Kauffman, C. A., Fenical, W. 2006. Daryamides A-C, Weakly Cytotoxic Polyketides from a Marine-Derived Actinomycete of the Genus *Streptomyces* strain CNQ-085 *J. Nat. Prod.* 69:1756-1759.

Arena, J. P., K. K. Liu, et al. (1995). "The mechanism of action of avermectins in *Caenorhabditis elegans*—correlation between activation of glutamate-sensitive chloride current, membrane binding and biological activity." *Journal of Parasitology* 81: 286-294.

Byrom, D. (1991). "Copolymer production." EP 0431883 A2.

Duràn, N., G. Z. Justo, et al. (2007). "Minireview. Violacein: properties and biological activities." *Biotechnol. Appl. Biochem.* 48: 127-133.

Duràn, N. and C. F. M. Menck (2001). "*Chromobacterium violaceum*: a review of pharmacological and industrial perspectives." *Crit. Rev. Microbiol.* 27: 201-222.

Furneaux, G. C. (2005). "Compostable packaging material and method." WO 030482 A1.

Hahn, S. K.; Chang, Y. K.; Lee, S. Y. (1995). Recovery and characterization of poly(3-hydroxybutyric Acid) synthesized in *Alcaligenes eutrophus* and recombinant *Escherichia coli*. *Applied & Environ. Microbiol.* 61, 34-39.

Hoshino, T., T. Takano, et al. (1987). "Biosynthesis of violacein: origins of the hydrogen, nitrogen and oxygen atoms in the 2-pyrrolidone nucleus." *Agric. Biol. Chem.* 51: 2733-2741.

Huismar, G. W.; Peoples, O. P.; Skraly, F. A. (2000). "Transgenic microbial polyhydroxyalkanoate producers." WO 11188 A1.

Huismar, G. W.; Skraly, F. A.; Martin, D. P.; Peoples, O. P. (1999). "Biological systems for manufacture of polyhydroxyalkanoate polymers containing 4-hydroxyacids." WO 14313 A2.

Hungria, M., S. Astolfi-Filho, et al. (2005). "Genetic characterization of *Chromobacterium* isolates from black water environments in the Brazilian Amazon." *Lett. Appl. Microbiol.* 41: 17-23.

Khanna S, Srivastava A K. (2005). "Recent advances in microbial polyhydroxyalkanoates" *Process Biochemistry"* 40, 607-619.

Krans R G, Gabbert K K, Locke T A, Madigan M T (1997). "Polyhydroxyalkanoate production in *Rhodobacter capsulatus*: Genes, mutants, expression, and physiology." *Appl. Environ. Microbiol.* 63, 3003-3009.

Krieg, A., A. M. Huger, et al. (1983). "*Bacillus thuringiensis* var. tenebrionis: Ein neuer, gegenuber Larven von Coleopteren wirksamer Pathotyp." *Z. Angew. Entomol.* 96: 500-508.

Kämpfer, P., H.-J. Busse, et al. (2009). "*Chromobacterium piscinae* sp. nov. and *Chromobacterium pseudoviolaceum* sp. nov., from environmental samples." *Int. J. Syst. Evol. Microbiol.* 59: 2486-2490.

Lee, S. Y. (1996). "Bacterial polyhydroxyalkanoates". *Biotechnol. Bioeng.* 49, 1-14.

Martin, P. A. W., D. Gundersen-Rindal, et al. (2007a). "*Chromobacterium substugae* sp. nov., a betaproteobacterium toxic to Colorado potato beetle and other insect pests." *Int. J. Syst. Evol. Microbiol.* 57: 993-999.

Martin, P. A., A. D. S. Shropshire, et al., (2007b). "*Chromobacterium substugae* sp. nov for control of insect pests" U.S. Pat. No. 7,244,607 B2.

Martin, P. A. W., Hirose, E., and Aldrich, J. R. 2007c. "Toxicity of *Chromobacterium substugae* to southern green stink bug (Heteroptera:Pentatomidae) and corn rootworm (Coleoptera:Chrysomelidae)". *J. Econ. Entomol.* 100: 680-684.

Martin, P. A. W., Blackburn, M., et al. (2004), "Two New Bacterial Pathogens of Colorado Potato Beetle (Colorado: Chrysomelidae)", *J. Econ. Entomol.* 97:774-780 (2004).

Martin, P. A. W., "A Freeze-Dried Diet to Test Pathogens of Colorado potato beetle", *Biological Control* 29:109-114 (2004).

Maskey, R. M.; Kock, I.; Shaaban, M.; Grun-Wollny, I.; Helmke, E.; Mayer, F.; Wagner-Dobler, I.; Laatsch, H. (2002) Low molecular weight oligo-B-hydroxybutyric acid and 3-hydrox-N-phenyl-butyramide new products from microorganism. *Polymer bulletin.* 49, 87-93.

McClean, K. H., M. K. Winson, et al. (1997). "Quorum sensing and *Chromobacterium violaceum*: exploitation of violacein production and inhibition for the detection of N-acyl homoserine lactones" *Microbiology* 143: 3703-3711.

Mukhopadhyay M., Patra A., Paul, A. K., (2005). "Production of poly(3-hydroxybutyrate) and poly(3-hydroxybutyrate-co-3-hydroxy-valerate)" by *Rhodopsudomonas palustris* SP5212" *J. Micro. Biotech.*, 21, 765-769.

Peoples, O. P.; Sinskey, A. J. (1991). "Method for producing novel polyester biopolymer." WO 910091 A1.

Reddy, C. S. K.; Ghai, R.; Kalia, R. V. C. (2003). "Polyhydroxyalkanoates: an overview" *Bioresource Technology."* 87, 137-146.

Ryan, K. S. and C. L. Drennan (2009). "Divergent pathways in the biosynthesis of bisindole natural products." Chemistry & Biology 16: 351-364.

Thompson, G. D., R. Dutton, et al. (2000). "Spinosad—a case study: an example from a natural products discovery programme" *Pest Management Science* 56: 696-702.

Young, C.-C., A. B. Arun, et al. (2008). "*Chromobacterium aquaticum* sp. nov., isolated from spring water samples." *Int. J. Syst. Evol. Microbiol.* 58: 877-880.

What is claimed is:

1. A method for modulating infestation of a pest, wherein said pest is selected from an Acari, Muscidae, Drosophilidae, Anthomyidae, Aphididae, Triozidae, Tenebrionidae, and Scarabaeidae, in a location where modulation is desired comprising the step of: applying an amount of a composition comprising a supernatant of a whole cell broth, a filtrate of a whole cell broth, an extract of a whole cell broth or a whole cell broth collected from *Chromobacterium subtsugae* Nov strain (NRRL B-30655) fermentation, effective for modulating said infestation.

2. The method according to claim 1, wherein the location where modulation is desired is on a plant, plant seed or in soil.

3. The method according to claim 1, wherein said pest is an Acari and the Acari is a mite.

4. The method according to claim 3, wherein said mite is a *Tetranychus* sp.

5. The method of claim 4, wherein the *Tetranychus* sp. is *Tetranychus urticae.*

6. The method according to claim 1 wherein said pest is selected from a *Musca* sp., *Myzus* sp., *Bactericera* sp., *Cyclocephala* sp., *Alphitobius* sp., *Drosophila* sp., *Delia* sp., *Rhizotrogus* sp., *Popillia* sp., *Anomala* sp., and *Otiorhynchus* sp.

7. The method according to claim 1, wherein said pest comprises *Musca domesitcas, Drosophila suzukii, Delia radicum, Myzus persicae, Bactericera cockerelli, Alphitobius diaperinusxi, Cyclocephala lurida, Rhizotrogus majalis, Popilla japonica, Otiorhynchus sulcatus*, or *Anomala orientalis.*

8. The method of claim 1, wherein the pest is a Scarabaeidae larva.

9. The method of claim 1, wherein the composition comprises supernatant, filtrate, or extract from the whole cell broth.

10. A method for modulating infestation of a pest, wherein said pest is selected from an Acari, Muscidae, Drosophilidae, Anthomyidae, Aphididae, Triozidae, Tenebrionidae, and Scarabaeidae, in a location where modulation is desired comprising the step of:

applying an amount of a composition comprising a whole cell broth collected from *Chromobacterium subtsugae* Nov strain (NRRL B-30655) fermentation comprising violacein, deoxyviolacein, and/or chromamide A, effective for modulating said infestation.

* * * * *